United States Patent [19]

Plotnikoff

[11] Patent Number: 4,801,614

[45] Date of Patent: Jan. 31, 1989

[54] PROCESS FOR USING ENDOGENOUS ENKEPHALINS AND ENDORPHINS TO INHIBIT GROWTH OF TUMEROUS CELLS

[75] Inventor: Nicholas P. Plotnikoff, Tulsa, Okla.

[73] Assignee: TNI Pharmaceuticals, Inc., Tulsa, Okla.

[21] Appl. No.: 105,491

[22] Filed: Oct. 1, 1987

Related U.S. Application Data

[63] Continuation of Ser. No. 928,721, Nov. 7, 1986, which is a continuation of Ser. No. 698,037, Feb. 4, 1985, which is a continuation-in-part of Ser. No. 597,378, Apr. 6, 1984, Pat. No. 4,537,878, which is a continuation-in-part of Ser. No. 308,287, Oct. 5, 1981, abandoned.

[51] Int. Cl.$^4$ .............................................. A61K 37/02
[52] U.S. Cl. ...................................... 514/17; 530/809
[58] Field of Search ................... 530/302, 809; 514/17

[56] References Cited

U.S. PATENT DOCUMENTS 4,537,878 8/1985 Plotnikoff ........................... 530/302

OTHER PUBLICATIONS

Chem. Absts. vol. 96, (1982) 29203m.
Chem. Abstr. vol. 100, (1984) 173021u.
Internat'l Symposium on New Trends in human Immun & Cancer Immunotherapy (1980)48–55.

Primary Examiner—Delbert R. Phillips
Attorney, Agent, or Firm—Robert B. Stevenson

[57] ABSTRACT

A process for the therapeutic treatment of cancer patients involving stimulation and promotion of the natural immune system (both T cell and NK cell activity) resisting and inhibiting tumorous growth (cancer) as well as resisting infections (viral, bacterial and fungal) by administering an effective dosage (e.g., 0.25 mg per kilogram of body weight to as low as about $10^{-14}$ mg/kg) of an endogenous endorphin (e.g., leucine-enkephalin and methionine-enkephalin).

24 Claims, 4 Drawing Sheets

PROCESS FOR USING ENDOGENOUS ENKEPHALINS AND ENDORPHINS TO INHIBIT GROWTH OF TUMEROUS CELLS

CROSS-REFERENCE TO RELATED APPLICATIONS

This is a continuation of co-pending application Ser. No. 928,721, filed on 11/7/86, which is a continuation of copending application Ser. No. 698,037 filed on Feb. 4, 1985, which is a continuation-in-part of Ser. No. 597,378 filed on Apr. 6, 1984, now U.S. Pat. No. 4,537,878, which is a continuation-in-part of Ser. No. 308,287 filed on Oct. 5, 1981, now abandoned.

BACKGROUND OF THE INVENTION

1. Field of the Invention

This invention relates to a process of stimulating and promoting the natural immune system (T cells and NK cells) resisting and inhibiting the growth of tumorous cells as well as resisting infections (virus, bacteria, fungi). More specifically, this invention relates to the in vivo use of leucine-enkephalin and methionine-enkephalin or the like as a therapeutic treatment for cancer.

2. Description of the Prior Art

Since the discovery, isolation and the complete analysis of the amino acid sequence of specific, endogenous, highly reactive and incredibly powerful peptides (e.g., interferon, endorphins and enkephalins), a rebirth and revitalization of interest and activity of biochemical research has taken place. During the last decade, the industrial world's race to be the first to commercially synthesize interferon is not only a daily topic on Wall Street, but is also well known to the layman and casual observer. Perhaps as at no other time in history has the phrase "the miracles of modern medicine" been more applicable as a genuine expectation.

Consistent with the contemporary so-called 'lock and key' theory, the existence of specific receptors in the brain for morphine-like substances has been established and corresponding endogenous specific ligands have been located and identified as to be two pentapeptides, methionine-enkephalin and leucine-enkephalin (Hughes et al, Nature, 258 577–579 (1975); Simatov et al, Proc. Natl. Acad., Sci., U.S.A., 73 2515–2519 (1976); Kosterlitz, *Opiates and Endogenous Opioid Peptides*, Elsevier/North Holland Biomedical Press (1976)). Other larger peptides, the endorphins, have also been found to bind to morphine receptors (Li et al, Nature, 260 622–24 (1976); Cox et al, Proc. Natl. Acad. Sci., U.S.A., 73 1821–23 (1976); Segal et al, Science 198 411–413 (1977)). Subsequent studies elaborated on the analgesic activity in various animal models by the intracerebral route of administration. However, there appeared to be a lack of analgesic activity when the peptides were administered by the intravenous (or intramuscular or intraperitoneal) routes of administration. This dichotomy of analgesic activity by different routes of administration (brain versus peripheral) was explained in terms of blood-brain barrier differences as well as a rapid rate of metabolism in plasma.

However, pronounced activity by systemic administration was discovered by Plotnikoff et al (Life Sc. 19 1283–1288 (1976)), who showed that the enkephalins-endorphins exhibited marked activity as tranquilizers and antidepressants. Most important, Plotnikoff demonstrated that the enkephalins were extremely active in potentiating the central effects of dopamine.

In 1979, Wybran et al reported that normal human blood T lymphocytes bear surface receptor-like structures for methionine-enkephalin and recent discoveries further support the view that T-cell lymphocytes were covered with enkephalin and endorphin receptor sites.

In the same year, the New York Academy of Sciences Symposium on Subcellular Factors in Immunity (Volume 332, Dec. 28, 1979) disclosed that the thymus gland of animals and humans was secreting peptides (thymosin and others) that controlled activities of T-cell lymphocytes and associated cells. These thymus peptides were found to have anti-neoplastic effects in animals and humans. In addition, the thymus peptides were found to control the aging process. Finally, the thymus peptides appear to regulate 'auto-immune response' of lymphocyte particles.

SUMMARY OF THE INVENTION

In view of the above, I have discovered a process for stimulating the natural immune system resisting tumorous growth and infections (viruses, bacteria and fungi) comprising the step of treating the tumorous growth and infections, in vivo, with an endogenous enkephalin. Thus, the present invention provides a process for the therapeutic treatment of cancer patients by administering an effective dosage of endogenous endorphin and/or enkephalin. The invention further provides that the endogenous enkephalin be leucine-enkephalin or methionine-enkephalin and that they be administered at a dosage rate from about a quarter of a miligram of enkephalin per kilogram of body weight to as low as about $10^{-14}$ mg/kg.

It is an object of the present invention to provide a process for the use of naturally occurring peptides to promote and stimulate the immune system's resistance to neoplastic cellular growth and infection. It is a further object to provide a process for using, in vivo, leucine-enkephalin and methionine-enkephalin to stimulate the natural immune system's anti-neoplastic, anti-viral, anti-bacterial, anti-fungal and anti-parasitic activity, particularly in cancer patients. Fulfillment of these objects and the presence and fulfillment of other objects will be apparent upon complete reading of the specification and claims.

DESCRIPTION OF THE PREFERRED EMBODIMENT

Figure 1:
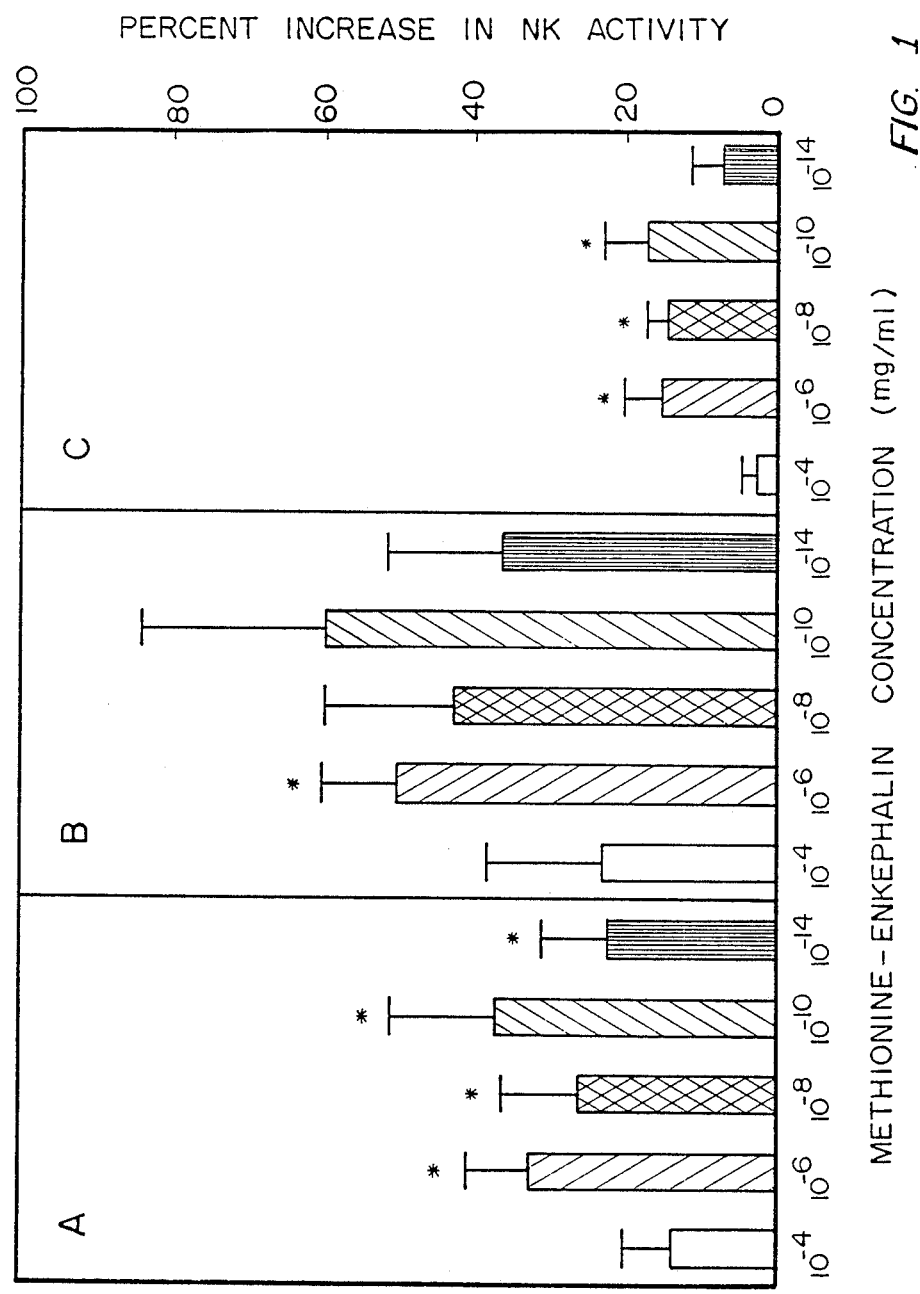
FIG. 1 illustrates the in vivo effect of methionine-enkephalin on the NK cell activity of human blood from normal volunteers.
Figure 2:
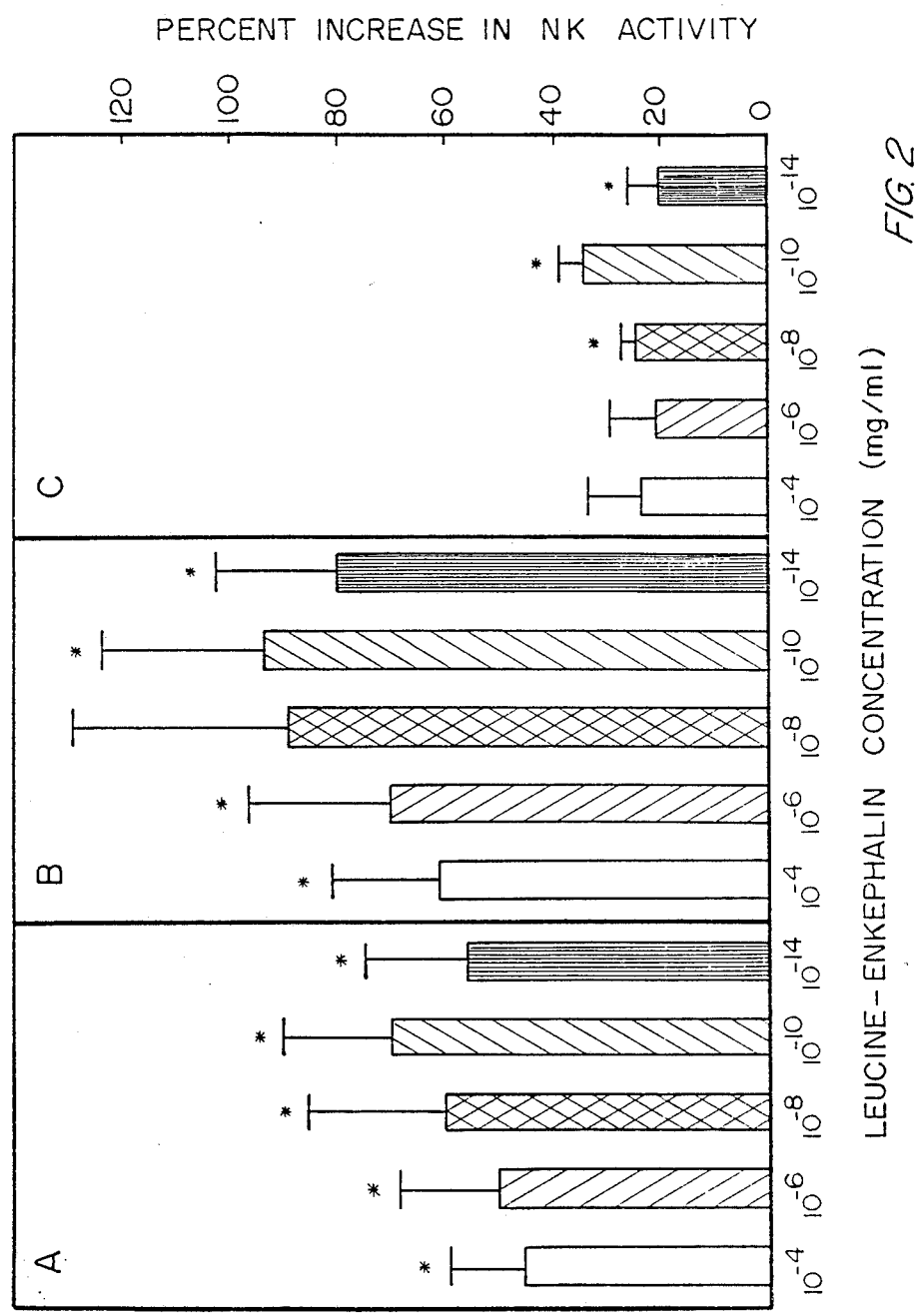
FIG. 2 illustrates the in vivo effect of leucine-enkephalin on the NK cell activity of human blood from normal volunteers.

Starting with the two facts: (1) T-cell lymphocytes are covered with enkephalin and endorphin receptors and (2) the thymus gland of animals and humans secretes peptides (thymosin and others) that control the activities of T-cell lymphocytes and associated cells, I propose a working hypothesis that the hypothalamus secretes the releasing factor (corticotrophin releasing factor-CRF) to the pituitary gland (storehouse of beta-endorphin and ACTH). Therefore, the beta-endorphins' and ACTH's release are controlled by factors from the hypothalamus. The release of beta-endorphin and ACTH from the pituitary results in stimulation of the thymus and adrenals releasing enkephalins and endorphins and the entire immune cascade of responses. Beta-endorphin is probably also metabolized in the bloodstream into its numerous fragments (alpha- and gamma-endorphin as well as the smaller enkephalins). These smaller fragments are active in stimulating the immune systems.

In order to test the hypothesis and to establish the efficacy of these smaller fragments, the following series of in vivo experiments were designed and performed, using laboratory mice inoculated with tumorous cells and then treated with leucine-enkephalin and methionine-enkephalin. Groups of $BDF_1$ female mouse strain (16-20 gms) were inoculated with L1210 (leukemia) tumor cells ($1 \times 10^4$, $1 \times 10^3$, or $1 \times 10^2$ cells) and observed for survival. The L1210 line of tumor cells was maintained in DBA/2 host mice. Ascitic fluid from the DBA/2 mice was used to inoculate the $BDF_1$ mice transferred in RPMI 1640 buffer at pH 8-9).

EXAMPLE I

Three separate experiments were conducted utilizing ten mice per group. The first experiment involved inoculating all mice with $1 \times 10^4$ cells, the second with $1 \times 10^3$ cells, and the third with $1 \times 10^2$ cells. Control groups were administered vehicle subcutaneously daily, while the methionine-enkephalin groups and the leucine-enkephalin groups were administered 10 mg/kg s.c. daily. The survival rate of the mice was monitored and the corresponding data for the three experiments are presented in TABLES I, II, and III repectively.

TABLE I $1 \times 10^4$ L1210 Tumor Cells in $BDF_1$ Mice - Effects of Enkephalins

| Days | Methionine-Enkephalin 10 mg/kg s.c.* | Controls | Leucine-Enkephalin 10 mg/kg s.c.* |
|---|---|---|---|
| 11 | 6 died | 5 died | 8 died |
| 12 | 1 died | 2 died | 0 died |
| 13 | 2 died | 3 died | 2 died |
|    | 9/10 died | 10/10 died | 10/10 died |

*Enkephalin injections started on day 2

TABLE II $1 \times 10^3$ L1210 Tumor Cells in $BDF_1$ Mice - Effects of Enkephalins

| Days | Methionine-Enkephalin 10 mg/kg s.c. | Controls | Leucine-Enkephalin 10 mg/kg s.c. |
|---|---|---|---|
| 13 | 0 died | 2 died | 2 died |
| 14 | 4 died | 2 died | 4 died |
| 15 | 3 died | 5 died | 0 died |
| 16 | 1 died | 1 died | 3 died |
| 17 | 1 died | 0 died | 0 died |
| 18 | 1 died | 0 died | 1 died |
|    | 10/10 died | 10/10 died | 10/10 died |

TABLE III $1 \times 10^2$ L1210 Tumor Cells in $BDF_1$ Mice - Effects of Enkephalins

| Days* | Methionine-Enkephalin 10 mg/kg s.c. | Controls | Leucine-Enkephalin 10 mg/kg s.c. |
|---|---|---|---|
| 15 | 3 died | 5 died | 1 died |
| 16 | 2 died | 1 died | 1 died |
| 17 | 2 died | 1 died | 0 died |
| 18 | 0 died | 1 died | 1 died |
| 19 | 1 died | 0 died | 0 died |
| 20 | 1 died | 1 died | 0 died |
| 21 | 0 died | 0 died | 0 died** |
|    | 9 died | 9 died | 3 died |

*Enkephalin injections started on day two
**Chi square test p < 0.025 between controls and leucine-enkephalin With the high tumor cell count of $1 \times 10^4$, no differences in survival times between controls, methionine-enkephalin, or leucine-enkephalin treated groups were seen (TABLE I). In the experiment in which the mice were inoculated with $1 \times 10^3$ tumor cells (TABLE II), survival time for the controls was 16 days, 18 days for the methionine-enkephalin group, and 18 days for the leucine-enkephalin treated group. However, in the third experiment, carried out at $1 \times 10^2$ tumor cells, the survival time for the controls as well as the methionine-enkephalin treated group was 20 days, while the leucine-enkephalin group had a survival time of >20 days.

The seven surviving mice from experiment three were continued on daily leucine-enkephalin medication (10 mg/kg i.p.) until day 36. The mice did not receive any additional leucine-enkephalin medication on subsequent days of the experiment. On day 37, the surviving seven mice were rechallenged with an additional inoculum of tumor cells ($1 \times 10^4$ cells) One of the seven mice so treated died on day 52. The remaining six mice survived until day 64, at which time they were rechallenged further with a higher inoculum of tumor cells ($1 \times 10^6$). All six mice died by day 70. These rechallenge studies suggest that leucine-enkephalin is stimulating the immune system as measured by survival of the test animals.

EXAMPLE Ia

The previous third experiment with $1 \times 10^2$ L1210 tumor cells was repeated two more times to increase the total number of mice to thirty per group, thus enhancing the statistical reliability of the results. The composite results of the three runs are presented below in TABLE IIa. Again, a statistically significant difference determined by the Chi square test (p<0.05) was found between the leucine-enkephalin treated group and the control group corresponding to direct experimental evidence of extraordinary stimulation of the immunity systems.

TABLE IIa $1 \times 10^2$ Tumor Cells in $BDF_1$ Mice

| Days | Methionine-Enkephalin 10 mg/kg s.c. | Controls | Leucine-Enkephalin 10 mg/kg s.c. |
|---|---|---|---|
| 14 | 1/30 Died | 1/30 Died | — |
| 15 | 10/30 | 12/30 | 5/30 Died |
| 16 | 18/30 | 21/30 | 13/30 |
| 17 | 25/30 | 24/30 | 15/30 |
| 18 | 25/30 | 25/30 | 16/30 |
| 19 | 26/30 | 26/30 | — |
| 20 | 27/30 | 27/30 | — |

TABLE IIa-continued

| | 1 × 10² Tumor Cells in BDF₁ Mice | | |
|---|---|---|---|
| Days | Methionine-Enkephalin 10 mg/kg s.c. | Controls | Leucine-Enkephalin 10 mg/kg s.c. |
| 21 | 27/30 | 27/30 | — |
| Total | 27/30 | 27/30 | 16/30** |

**Significant difference from controls $p < 0.05$ Chi square test.

EXAMPLE Ib

The above experiments were repeated again using $1 \times 10^2$ L1210 tumor cells with 30 mg/kg dosage rate of methionine-enkephalin to a group of thirty mice. The results as presented in TABLE IIb confirmed a statistically significant difference between the methionine-enkephalin treated group and the control group at this high dosage rate.

TABLE IIb

| | 1 × 10² Tumor Cells | |
|---|---|---|
| Days | Controls | Methionine-Enkephalin 30 mg/kg |
| 13 | — | 1 |
| 14 | 2 | 4 |
| 15 | 20 | 15 |
| 16 | 35 | 20 |
| 17 | 41 | 22 |
| 18 | 43 | 23 |
| 19 | 44 | — |
| 20 | 0 | — |
| 21 | 0 | — |
| 22 | — | 24 |
| | 44/49 Dead ED50 = 15 ± 0.4 days | 24/30 Dead ED50 = 18 ± 1.2 days** |

**Significant difference from control $p < 0.05$ Chi square test.

EXAMPLE II

A second set of three experiments was performed in a manner similar to the experiments of EXAMPLE I except that 25 mice were used as controls, 30 mice were treated with methionine-enkephalin and another 30 were treated with leucine-enkephalin. In each case the mice were inoculated with $1 \times 10^4$ tumor cells and the enkephalin was administered daily at 30 mg/kg s.c. The data related to the survival of the mice are presented in TABLE IV.

TABLE IV

| | 1 × 10⁴ L1210 Tumor Cells in BDF₁ Mice - Effects of Enkephalins* | | |
|---|---|---|---|
| | # dead/# tested | | |
| Days | Controls | 30 mg/kg Methionine-Enkephalin | 30 mg/kg Leucine-Enkephalin |
| 13 | 7/25 | 5/30 | 3/30 |
| 14 | 10/25 | 7/30 | 5/30 |
| 15 | 16/25 | 8/30 | 12/30 |
| 16 | 20/25 | 12/30 | 17/30 |
| 17 | 21/25 | 15/30 | 22/30 |
| 18 | 21/25 | 18/30 | 22/30 |
| 19 | 21/25 | 18/30 | 26/30 |
| 20 | 22/25 | 19/30 | 26/30 |
| 21 | 22/25 | 19/30 | 26/30 |
| Total | 22/25 | 19/30** | 26/30 |

*Pooled three experiments
**Significant difference from controls $p < 0.05$ Chi square test As indicated in TABLE IV, approximately half the control mice died by the fourteenth day. In contrast, half of the methionine-enkephalin treated mice died by the seventeenth day. By day 21 of the experiment, eleven out of the thirty treated mice had survived. Delayed deaths were also seen in mice treated with leucine-enkephalin. The median day of death was about sixteen days. Thus, the last three experiments (EXAMPLE II) demonstrate that the higher doses of both leucine- and methionine-enkephalin (30 mg/kg) are effective in prolonging survival of mice inoculated with $1 \times 10^4$ cells. Of great interest is the apparent potency of methionine-enkephalin, resulting in survival at day 21 of 11 of 30 mice. This survival finding may be related to and be consistent with the previous observation that specific receptor binding sites for the enkephalins are present on T lymphocytes.

A dramatic increase in survival time of the leucine-enkephalin treated mice in the third experiment of EXAMPLES I and Ia and the sharp contrast of these leucine-enkephalin treated mice when compared both to the control mice and to the methionine-enkephalin treated mice (9 out of 10 expired between days 14–20), can be seen when comparing the results of the third experiment to those of the first and second experiments of EXAMPLE I (TABLES I–III). This indicates that there is remarkable and sharp separation in the activities of leucine- versus methionine-enkephalin at lower inoculation rates ($1 \times 10^2$ cells) and these effects persist even after rechallenging with tumor cells. This is again consistent with the original hypothesis and also suggests that leucine-enkephalin plays a neuroendocrine messenger role between the central nervous system and the immune system.

EXAMPLE III

In order to test for any synergistic effect of using an endogenous enkephalin with a known chemotherapeutic agent, a study involving the inoculation of groups of mice with massive doses ($1 \times 10^6$) of L1210 tumor cells was performed in a manner analogous to the previous examples transferred in RPMI 1640 at pH 7. Three different concentrations of cis-platin, with and without methionine-enkephalin treatment, were administered and compared to a control involving neither cis-platin nor methionine-enkephalin. The following TABLES V, VI, and VII represent the results of this study. Statistical analysis of the data by the Chi square test confirms that cis-platin (the chemo-therapeutic agent) exhibits significant statistical delay of the rate of onset of mortality relative to the control and that the combination of methionine-enkephalin treatment with cis-platin exhibits a statistically significant delay in the mortality rate relative to the use of cis-platin by itself and that the significance of the statistical trend is enhanced as time progresses.

TABLE V

| | 1 × 10⁶ L1210 Tumor Cells In BDF₁ Mice - Single Dose of 8 mg/Kg cis-platin 30 mg/Kg s.c. Methionine-Enkephalin | | |
|---|---|---|---|
| Days | Cis-platin and Methionine-Enkephalin | Saline Control | Cis-platin |
| 8 | | 10/20 | |
| 9 | | 19/20 | 2/20* |
| 10 | | 20/20 | |
| 11 | | | |
| 12 | 1/20* | | 4/20* |

TABLE V-continued $1 \times 10^6$ L1210 Tumor Cells In
BDF$_1$ Mice - Single Dose of
8 mg/Kg cis-platin
30 mg/Kg s.c. Methionine-Enkephalin

| Days | Cis-platin and Methionine-Enkephalin | Saline Control | Cis-platin |
|---|---|---|---|
| 13 | 3/20* | | 7/20** |
| 14 | 7/20* | | 12/20** |
| 15 | 13/20** | | 16/20 |
| 16 | 16/20 | | 18/20 |
| 17 | 18/20 | | |
| 18 | | | 19/20 |
| 19 | | | |
| 20 | | | 20/20 |
| 21 | 19/20 | | |

Median Day of Death ± s.e.

| ED50 | ED50 | ED50 |
|---|---|---|
| 16 day ± 0.6 | 8 days ± 0.3 | 12 Days ± 0.8 |

*Chi square test p < 0.05 significant difference
**Chi square test p < 0.10

TABLE VI $1 \times 10^6$ Tumor Cells
4 mg/Kg Cis-platin and
30 mg/Kg s.c. Methionine-Enkephalin

| Days | Cis-platin and Methionine-Enkephalin | Saline Control | Cis-platin |
|---|---|---|---|
| 8 | | 8/20 | |
| 9 | | 17/20 | |
| 10 | 1/20 | 19/20 | |
| 11 | 6/20* | 20/20 | 10/20* |
| 12 | 13/20** | | 15/20 |
| 13 | 19/20 | | 19/20 |
| 14 | | | |
| 15 | 20/20 | | 20/20 |

Median Day of Death ± S.E.

| ED50 | ED50 | ED50 |
|---|---|---|
| 12 Days ± 0.5 | 8 Days ± 0.3 | 10 Days ± 0.5 |

Significant difference from controls
*Chi square test p < 0.05
**Chi square test p < 0.10

TABLE VII $1 \times 10^6$ Tumor Cells
2 mg/Kg Cis-platin and
30 mg/Kg s.c. Methionine-Enkephalin

| Days | Cis-platin and Methionine-Enkephalin | Saline Control | Cis-platin |
|---|---|---|---|
| 8 | | 9/30 | |
| 9 | 1/20* | 12/30 | 3/20* |
| 10 | 6/20* | 18/30 | 13/20* |
| 11 | 11/20* | 20/30 | 14/20* |
| 12 | 14/20** | 23/30 | 15/20** |
| 13 | 16/20 | 25/30 | 17/20 |
| 14 | 18/20 | 29/30 | 19/20 |
| 15 | 20/20 | | |
| 16 | | 30/30 | |
| 17 | | | |
| 18 | | | |

Median Day of Death ± s.e.

| ED50 | ED50 | ED50 |
|---|---|---|
| 11 Days ± 0.6 | 9 Days ± 0.6 | 10 Days ± 0.7 |

Significant difference from controls
*Chi square test p < 0.05
**Chi square test p < 0.10

EXAMPLE IV

In order to further demonstrate the immune system stimulating characteristics of leucine-enkephalin and methionine-enkephalin, a Phytohemagglutinin (PHA) stimulated mouse lymphocyte blastogenesis study was performed. The effects of methionine- and leucine-enkephalin on PHA stimulated lymphocyte transformation are presented in TABLES VIII and IX. The results presented in the study correlate well with previous mortality studies in mice inoculated with L1210 particularly with respect to the concentration dependence of methionine- and leucine-enkephalin stimulation effects as well as verify extraordinary immune system stimulation.

TABLE VIII

Methionine Enkephalin and Lymphocyte Blastogenesis
(mean counts/minute ± s.e.)

| | PHA (1:100) | PHA (1:250) | PHA (1:500) | PHA (1:750) |
|---|---|---|---|---|
| Controls | (11) 1458 ± 90 | (11) 5840 ± 553 | (11) 8737 ± 970 | (10) 7686 ± 337 |
| 1 mg/ml | (4) 4393 ± 664** | (4) 11807 ± 3526** | (4) 13405 ± 6755 | (4) 10678 ± 5634 |
| $10^{-1}$ mg/ml | (6) 5258 ± 990** | (6) 17378 ± 4352** | (6) 19321 ± 2684** | (6) 15791 ± 1829** |
| $10^{-2}$ mg/ml | (6) 3144 ± 500** | (6) 10516 ± 2838** | (6) 13794 ± 2855* | (6) 10779 ± 1018** |
| $10^{-4}$ mg/ml | (6) 2123 ± 228** | (6) 7971 ± 1113* | (6) 10470 ± 1967 | (6) 9678 ± 1005** |
| $10^{-6}$ mg/ml | (6) 2357 ± 155** | (6) 7764 ± 912* | (6) 11208 ± 1941 | (6) 9164 ± 394** |
| $10^{-8}$ mg/ml | (4) 1884 ± 188** | (4) 8764 ± 2693 | (4) 11702 ± 3071 | (4) 8348 ± 99 |
| $10^{-10}$ mg/ml | (2) 1538 ± 170 | (2) 4237 ± 473 | (2) 6755 ± 742 | (2) 8324 ± 244 |

*p < 0.10 Significant difference from PHA controls
**p < 0.05 Significant difference from PHA controls
( ) = Number of individual samples quantified in liquid scintillation counter

TABLE IX

Leucine Enkephalin and Lymphocyte Blastogenesis
(mean counts/minute ± s.e.)

| | PHA (1:100) | PHA (1:250) | PHA (1:500) | PHA (1:750) |
|---|---|---|---|---|
| Controls | (11) 1458 ± 90 | (11) 5840 ± 553 | (11) 8737 ± 970 | (10) 7686 ± 337 |
| 1 mg/ml | (4) 1114 ± 310 | (4) 4411 ± 1945 | (4) 6752 ± 1200 | (4) 10589 ± 583* |
| $10^{-1}$ mg/ml | (6) 1516 ± 207 | (6) 5265 ± 1076 | (6) 9033 ± 356 | (6) 8543 ± 1203 |
| $10^{-2}$ mg/ml | (6) 1650 ± 180 | (6) 6154 ± 370 | (6) 10711 ± 1654 | (6) 10468 ± 1117** |
| $10^{-4}$ mg/ml | (6) 1918 ± 293* | (6) 8273 ± 1586* | (6) 13429 ± 2885* | (6) 9213 ± 675** |
| $10^{-6}$ mg/ml | (6) 2425 ± 323** | (6) 8764 ± 727** | (6) 13092 ± 2505* | (6) 10814 ± 985** |
| $10^{-8}$ mg/ml | (4) 2759 ± 387** | (3) 10710 ± 2142** | (4) 14052 ± 3403* | (4) 8719 ± 665 |

TABLE IX-continued

Leucine Enkephalin and Lymphocyte Blastogenesis
(mean counts/minute ± s.e.)

| | PHA (1:100) | PHA (1:250) | PHA (1:500) | PHA (1:750) |
|---|---|---|---|---|
| $10^{-10}$ mg/ml | (2) 2065 ± 360** | (2) 9825 ± 3575** | (2) 8074 ± 611 | (2) 8559 ± 52; |

*p < 0.10 Significant Difference from PHA Controls
**p < 0.05 Significant Difference from PHA Controls
( ) = Number of Individual Samples Quantified in Liquid Scintillation Counter

EXAMPLE V

In order to further demonstrate the cell mediated immunity system characteristics of the present invention, a series of in vitro tests were performed on human blood from normal volunteers. The study involved determining the active T-cell rosettes population (see further details of test procedure in Example VI) of the untreated blood and for treated blood at one of four concentrations of either leucine- or methionine-enkephalin addition as well as determining the total rosettes for both enkephalins at the four respective dosage levels. Data summarizing the study are presented in TABLES X through XIV. The data establishes that both leucine-enkephalin and methionine-enkephalin increased significantly the active T-cell rosettes of normal volunteers and that neither enkephalin alters total T-cell rosettes. It is concluded from the data that endogenous enkephalins play a role in cell mediated immunity and specifically T-cell function.

TABLE X

Methionine-Enkephalin - Percentages of Active T-Cell Rosettes

| | Untreated | Methionine-Enkephalin |
|---|---|---|
| $10^{-2}$ mg/cc. | 38.4 ± 5.6 | (9/11) 51.8 ± 4.8 |
| $10^{-6}$ mg/cc. | 31.9 ± 4.6 | (7/11) 47.9 ± 4.8* |
| $10^{-10}$ mg/cc. | 34.1 ± 5.3 | (9/11) 54.4 ± 3.9* |
| $10^{-14}$ mg/cc. | 36.6 ± 7.7 | (7/9) 48.3 ± 5.5 |

*Significant difference from matching controls p < 0.05
( ) = Number of samples in analyses with increased number of rosettes compared to total number analyzed

TABLE XI

Methionine-Enkephalin - Subjects with Depressed Active T-Cell Rosettes

| | Untreated | | Methionine-Enkephalin |
|---|---|---|---|
| $10^{-2}$ mg/cc. | 20 | (2/11) | 18 |
|  | 27 |  | 15 |
| $10^{-6}$ mg/cc. | 20 | (4/11) | 14 |
|  | 59 |  | 30 |
|  | 64 |  | 34 |
|  | 27 |  | 25 |
| $10^{-10}$ mg/cc. | 59 | (2/11) | 46 |
|  | 27 |  | 20 |
| $10^{-14}$ mg/cc. | 31 | (2/9) | 24 |
|  | 27 |  | 12 |
|  | Totals = | 10/42 = 24%* | |

( ) = Number of individual samples with depressed levels compared to total number analyzed
*No significant difference between untreated and methionine-enkephalin values

TABLE XII

Leucine-Enkephalin - Percentages of Active T-Cell Rosettes

| | Untreated | Leucine-Enkephalin |
|---|---|---|
| $10^{-2}$ mg/cc. | 31.3 ± 4.8 (10/12) | 47.4 ± 3.8* |
| $10^{-6}$ mg/cc. | 32.4 ± 4.6 (10/12) | 45.9 ± 4.8 |
| $10^{-10}$ mg/cc. | 34.0 ± 6.7 (8/12) | 54.1 ± 5.1* |
| $10^{-14}$ mg/cc. | 32.7 ± 5.7 (9/12) | 54.0 ± 4.2* |

TABLE XII-continued

Leucine-Enkephalin - Percentages of Active T-Cell Rosettes

| | Untreated | Leucine-Enkephalin |
|---|---|---|
| Totals = | (37/48) = 77% | |

*Significant difference from matching controls
( ) Number of samples used in analyses with matching controls

TABLE XIII

Leucine-Enkephalin - Subject Samples with Depressed Active T-Cell Rosettes

| | Untreated | | Leucine-Enkephalin |
|---|---|---|---|
| $10^{-2}$ mg/cc. | 31 | (2/12) | 12 |
|  | 64 |  | 33 |
| $10^{-6}$ mg/cc. | 20 | (2/12) | 14 |
|  | 64 |  | 33 |
| $10^{-10}$ mg/cc. | 31 | (4/12) | 25 |
|  | 20 |  | 10 |
|  | 28 |  | 11 |
|  | 27 |  | 15 |
| $10^{-14}$ mg/cc. | 59 | (3/12) | 54 |
|  | 28 |  | 20 |
|  | 27 |  | 25 |
|  | Total = | (11/48) = 23%* | |

*No significant difference from controls p < 0.05
( ) Number of depressed samples

TABLE XIV

Total Rosettes (Means ± s.e.)

| | Methionine-Enkephalin | Leucine-Enkephalin |
|---|---|---|
| Untreated | 59.9 ± 3.1 | 59.9 ± 3.1 |
| $10^{-2}$ mg/cc. | 59.9 ± 3.4 | 60.3 ± 3.3 |
| $10^{-6}$ mg/cc. | 63.5 ± 2.7 | 58.0 ± 3.5 |
| $10^{-10}$ mg/cc. | 58.0 ± 3.5 | 63.0 ± 2.4 |
| $10^{-14}$ mg/cc. | 60.4 ± 3.4 | 60.9 ± 2.6 |

EXAMPLE VI

In a manner analogous to EXAMPLE V the active T-cell rosettes and total rosettes population of a series of human blood samples derived from lymphoma patients were measured. The clinical characteristics of the patients included in this study are outlined in TABLE XV. All patients had histologically diagnosed lymphoma, one with Hodgkin's disease and the remainder with nonHodgkin's lymphoma. The patients were considered to have advanced stages of disease at the time of study. One patient ("F") presented very bulky lymphadenopathy and was studied prior to and following the initiation of chemotherapy. 30 ml of heparinized blood was obtained from each of the patients and allowed to sediment. The leukocyte-rich plasma was collected and diluted twofold in phosphate-buffered saline (0.01M; pH 7.2). The diluted cell-rich plasma was layered over a Ficoll-Paque gradient cushion (Pharmacia, Piscataway, N.J.), centrifuged for 30 min at 400 g, the mononuclear band collected, washed twice, and resuspended in RPMI 1640 medium. The mononuclear cell fraction was evaluated for active and total T lymphocytes and the influence leucine-enkephalin and methionine-enkephalin had on the rosette process. The mononuclear cell fraction was first incubated with 25 μl of a 1/100 dilution of latex bead preparation/$10^6$ cells for 30 min at 37° C. in order that any phagocytic cells would engulf the latex beads and thus be easily identified under the microscope. The cells were washed twice and adjusted to $1 \times 10^7$ cells/ml in RPMI 1640 medium. A volume of 0.1 ml of cells was aliquoted into tubes along with 0.1 ml of varying dilutions of leucine-enkephalin and methionine-enkephalin incubated for 60 min at 37° C., and washed twice. The tubes designated for evaluation of active T cells received 0.1 m of RPMI 1640 medium to resuspend the pellet and 0.1 ml of fetal calf serum. The cells were allowed to incubate for another 60 min at 37° C., followed by the addition of $2 \times 10^7$ sheep red blood cells. The cell suspension was centrifuged at 200 g for 5 min, gently resuspended, and visually quantitated on an hemocytometer. The tubes designated for evaluation of total T cells received 0.1 ml of RPMI 1640 medium to resuspend the pellet, 0.1 ml of fetal calf serum, and $2 \times 10^7$ sheep red blood cells. The mixture was incubated at room temperature for 15 min, overnight at 4° C., and was returned to room temperature for 1 hr. The cell suspension was gently resuspended and visually quantitated on a hemocytometer. Any lymphocyte with three or more sheep red blood cells attached was considered a rosette. The results for the active or total T cells are reported as means and standard errors for the groups and statistical analyses were carried out by the Student t test. The enkephalins were purchased from CAL-MED, South San Francisco, Calif. (UCB Bioproducts, Brussels, Belgium) and reported to be chemically pure (>99%).

Significant increases in active rosettes were found when methionine-enkephalin ($10^{-2}$, $10^{-6}$, $10^{-10}$, and $10^{-14}$ mg/cc was added to lymphocytes taken from lymphoma patients (see TABLE XVI).

In sharp contrast to the positive enhancement effects of methionine-enkephalin, leucine-enkephalin was significantly effective only at one low concentration ($10^{-14}$ mg/cc) and the actual percentages of active rosettes are shown in TABLE XVI. It is apparent that methionine-enkephalin (at all concentrations tested) elevates active rosette formation.

Neither methionine-enkephalin nor leucine-enkephalin, at any concentration tested, had any significant effect on levels of total rosettes (TABLE XVII).

Untreated patient levels of 39.2±5.1 (for methionine-enkephalin) as well as 36.4±3.9 (for leucine-enkephalin) were found to be significantly different from untreated normal volunteers (54.8±4.5%), a value which is taken from our continuing comparative studies in normal volunteers.

The study demonstrated a significant enhancement of active T-cell rosettes with methionine-enkephalin from lymphoma patients. Lymphoma patients are considered to be immunosuppressed—both by the nature of their disease and as a result of treatment. The fact that our patients were found to have significantly less total T-cell rosettes than normal volunteers supports this contention. Comparative data on active T-cell rosettes in 100 normal subjects were reported to be 28.4±6.5% when, on the other hand, patients with cancer had levels of active T-cell rosettes in the range of 8–24% (depending on the status of disease) (see Wybran and Fudenberg, J. Clin. Invest. 52, 1026, 1973). The present study shows that untreated patient levels of active T-cell rosettes (27.6 and 32.0%) did not differ significantly from normal volunteer levels (28.4±6.5%). EXAMPLE V indicates methionine-enkephalin increases active T-cell rosettes in blood from normal volunteers, and the data of EXAMPLE VI indicate similar findings that confirm enhancement of active rosettes in immunosuppressed patients.

The relative lack of enhancement of the active T-cell rosettes by leucine-enkephalin at higher concentrations and a significant enhancement of active T-cell rosettes at a very low concentration ($10^{-14}$) suggests that specific enkephalin receptors ($\mu$ vs $\Delta$) may depress or stimulate active rosette formation as a function of dosage.

Further, the reduction of immunocompetence resulting from prolonged stress, in part, may be a result of depletion of enkephalin stores. The present study does support the idea that "replacement therapy" with the endogeneous ligand (methionine-enkephalin) or a closely related analog may be beneficial in restoring immunocompetence.

It is believed that the increase in active T-cell rosette-forming cells in our present study was a direct effect of nonmalignant population on T-cells because significant increases were seen in B-cell lymphoma and Hodgkin's disease.

Since the active T-cell rosette-forming cells represent a distinct subpopulation of T cells closely related to the overall level of cellular immunocompetence and since methionine-enkephalin is shown herein to enhance active T-cell rosettes in lymphoma patients, the present study postulates that immunomodulation by methionine-enkephalin provides a new approach to immunotherapy.

TABLE XV

| | | Patient Characteristics | | | |
|---|---|---|---|---|---|
| Patient | Age (years) | Diagnosis | Stage | Prior Therapy | Time of last treatment prior to test (weeks) |
| A | 51 | B-cell lymphoma | IV | Splenectomy | 52 |
| B | 83 | Non-Hodgkin's lymphoma | III | Cytoxan (Day 1) Vincristine (Day 1) Prednisone (Days 1–5) | 4 |
| C | 29 | Hodgkin's | IIIB | MOPP → ABVO → Total Nodal radiotherapy | 8 |
| D | 72 | Non-Hodgkin's lymphoma | IV | Cytoxan (Day 1) Vincristine (Day 1) Adriamycin (Days 1–5) Prednisone (Days 1–5) | 24 |
| E | 45 | Large-cell lymphoma | II | No therapy | — |

TABLE XV-continued

Patient Characteristics

| Patient | Age (years) | Diagnosis | Stage | Prior Therapy | Time of last treatment prior to test (weeks) |
|---|---|---|---|---|---|
| | 45 | Large-cell lymphoma | II | Cytoxan (Day 1) Vincristine (Day 1) Adriamycin (Day 1) Prednisone (Days 1-5) | 3-4 |

TABLE XVI

Percentages of Active Rosettes After Incubation

| Dose (mg) | Methionine-Enkephalin | Leucine-Enkephalin |
|---|---|---|
| Untreated | 27.6 ± 5.3 (5 determinations) | 32.0 ± 4.1 (8 determinations) |
| $10^{-2}$ mg | 46.6 ± 4.2* | 41.1 ± 5.6 |
| $10^{-6}$ mg | 49.0 ± 4.6* | 42.5 ± 3.3 |
| $10^{-10}$ mg | 46.8 ± 3.0* | 40.3 ± 5.7 |
| $10^{-14}$ mg | 48.5 ± 5.6* | 52.7 ± 2.8* |

*Significant difference from untreated samples, $p < 0.05$

TABLE XVII

Total Rosettes

| Dose (mg) | Methionine-Enkephalin percentages | Leucine-Enkephalin percentages |
|---|---|---|
| Untreated | 39.2 ± 5.1 (5) | 36.4 ± 3.9 (8) |
| $10^{-2}$ mg | 35.0 ± 6.9 | 32.6 ± 4.6 |
| $10^{-6}$ mg | 42.2 ± 6.8 | 32.6 ± 5.6 |
| $10^{-10}$ mg | 36.5 ± 6.5 | 37.6 ± 6.1 |

EXAMPLE VII

In order to illustrate the promoting of the natural immune system resisting growth of tumorous cells, a study of the effects of methinione-enkephalin and leucine-enkephalin on the so-called "natural killer" or NK cell activity was performed. A series of isolated human peripheral blood lymphocytes from various types of cancer patients as well as normal volunteers were incubated with enkephalin at one of four dosage levels and the NK activity was determined at 100:1, 33:1 and/or 11:1 effector-to-target cell ratios.

All blood samples utilized in this study were obtained from human volunteers. All experiments were performed with freshly isolated lymphocytes. Blood (approximately 30 ml) was collected by standard anticubital venipuncture and diluted 1:1 with RPMI 1640 medium. This mixture was layered over Histopaque (Sigma Chemical Co. St. Louis, MO) and centrifuged at 400 g for 30 minutes. The lymphocyte layer was removed, resuspended in RPMI 1640 and incubated in plastic petri dishes for one hour at 37° C. in 5% $CO_2$ in air to remove adherent cells (macrophages). The lymphocytes were then washed with RPMI 1640 and adjusted to a concentration of $1 \times 10^7$ cells/ml. Viability was determined by trypan blue exclusion, and was always greater than 98 percent.

The K-562 tumor cell line, a myeloid cell line derived from a pleural effusion of a patient with a chronic myelocytic leukemia in blast crisis, was used as the target cell in these studies. The start for this cell line was supplied by the National Cancer Institute.

The NK cell assays were performed as previously described in literature (see deLandazuri et al, *J. Immunology* 1981). Aliquots containing $2 \times 10^6$ target cells/ml were labeled with 150 μCi of $^{51}$Cr solution/ml of cells (Amerisham, Arlington Heights, IL) by incubation at 37° C. in 5% $CO_2$ in air for 45 minutes. After washing the cells 3 times, $5 \times 10^3$ viable cells in 0.1 ml of RPMI 1640 were pipetted into 96-well Linbro plates (Linbro Scientific, Hamden, CT). Various concentrations of effector cells in 0.1 ml of RPMI 1640 medium were added to triplicate wells to give effector:target ratios of 100:1, 33:1 and 11:1. After incubation at 37° C. in 5% $CO_2$ in air for 4 hours 100 μl of supernatant from each well was collected and counted for 2 minutes in a Beckman 4000 autogamma counter. The percentage of isotope released was used as a measure of cytotoxity and was calculated by the following formula:

$$\% \text{ specific release} = \frac{cpm \text{ experimental release} - cpm \text{ from medium control}}{cpm \text{ maximum release} - cpm \text{ medium control}} \times 100$$

where: *cpm* experimental release = counts released after incubation of target cells with effector cells.

*cpm* from medium control = counts spontaneously released by target cells incubated in medium alone.

*cpm* maximum release = counts released by lysis of target cells with 1% Triton X-100.

Both methionine-enkephalin and leucine-enkephalin were purchased from Peninsula Laboratories, Inc. (San Carlos, CA) as synthesized, chemically pure preparations. Aliquots of peripheral blood lymphocytes prepared as above were incubated for one hour at 37° C. in 5% $CO_2$ in air with an equal volume of varying dilutions ($10^{-4}$, $10^{-6}$, $10^{-8}$, $10^{-10}$, and $10^{-14}$ mg/ml) of either methionine-enkephalin or leucine-enkephalin. At the end of the incubation period the lymphocytes were washed with RPMI-1640 medium three times, resuspended in RPMI-1640 medium and utilized in NK cell assays.

The comparison of differences between treatment groups and non-treated cells was accomplished by the paired difference test.

The data corresponding to this in vitro study is presented in TABLES XVIII and XIX and FIGS. 1 through 4 of the drawing. The data presented in FIGS. 1 and 2 correspond to the normal volunteers while TABLES XVIII and XIX and FIGS. 3 and 4 correspond to cancer patients. The population of the volunteers used in the study fell into two groups with respect to spontaneous NK activity. Categorically the volunteers started from either a high initial NK activity or they had a relatively low initial NK activity. Thus the data presented in the FIGURES is analyzed as the population as a whole (legend A), the relatively low NK activity (legend B for FIGS. 1 and 2; legend C for FIGS. 3 and 4) and the relatively high NK activity (legend C for FIGS. 1 and 2; legend D for FIGS. 3 and 4) subgroups. The data illustrated in the FIGURES are from assays run at an effector-to-target cell ratio of 11:1 and are presented as percent increase in NK activity of nontreated cells from the same individual. In each case, the peripheral blood lymphocytes were treated with specified enkephalin at the concentrations shown for one hour and then assayed for NK activity. The stars indicate significant difference from nontreated cells ($p<0.05$).

As illustrated in FIG. 1, methionine-enkephalin enhanced NK cell activity of all concentrations tested. This enhancement was seen at all effector-to-target cell ratios investigated, but tended to be greatest in the 11:1 cell ratio. The enhancement induced by methionine-enkephalin tended to be biphasic with a dip in enhancement at the $10^{-8}$ mg/ml concentration. This tended to be the case with all individuals in the study and is reflected in the pooled data.

The observed percentage increase in NK activity following methionine-enkephalin treatment was higher in individuals with a naturally low NK activity, but only significant at one concetration ($10^{-6}$ mg/ml), while the percentage increase in activity was significant at three concentrations ($10^{-6}$, $10^{-8}$, and $10^{-10}$ mg/ml) in individuals with naturally high NK activity.

Treatment with leucine-enkephalin (FIG. 2) enhanced NK activity similarly to methionine-enkephalin. However, leucine-enkephalin was more active than methionine-enkephalin as evidenced by much greater percentage increases in NK activity following treatment with leucine-enkephalin. NK activity was significantly enhanced across the range of leucine-enkephalin concentrations in low activity individuals while only the three lowest concentrations induced significant changes in the high activity individuals.

Figure 3:
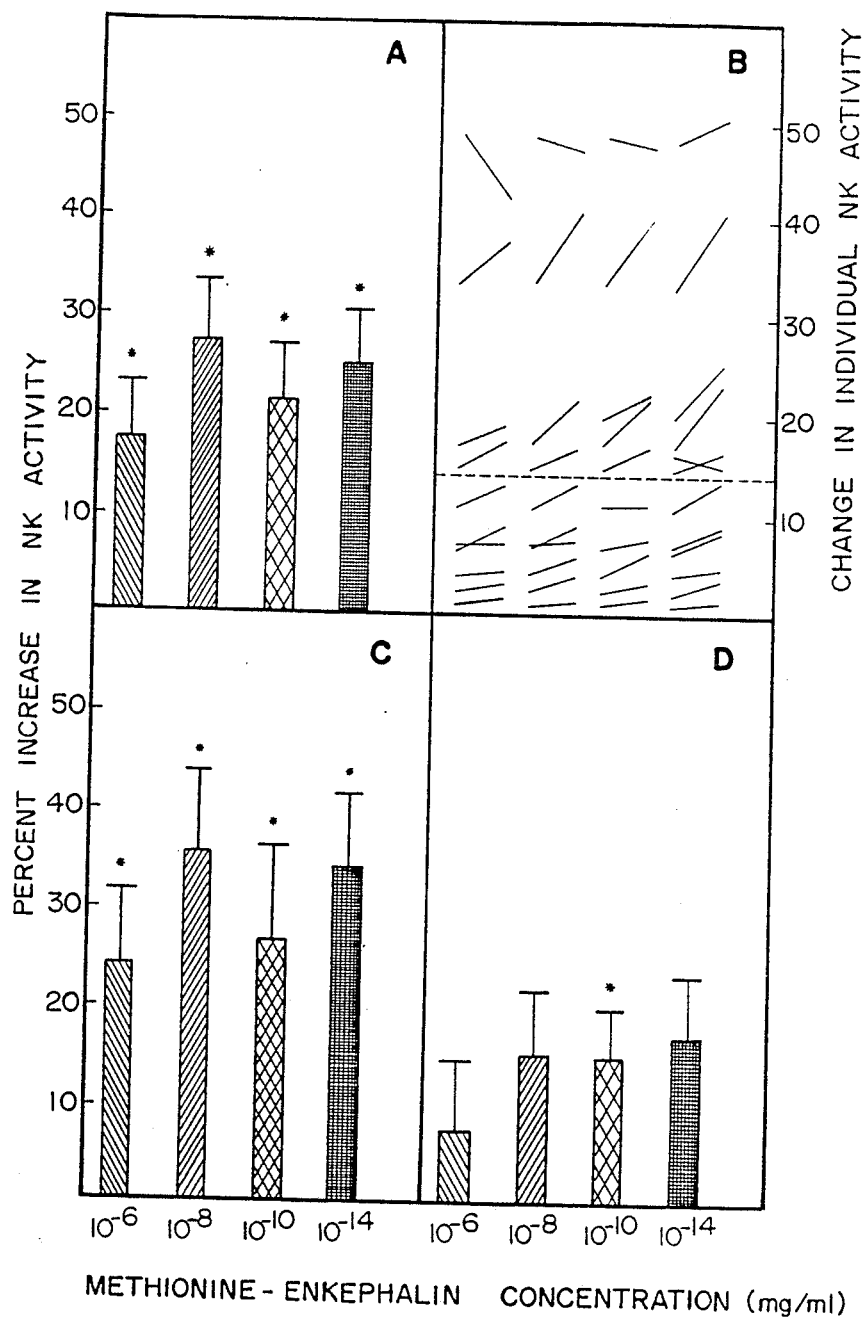
FIG. 3 illustrates the in vivo effect of methionine-enkephalin on the NK cell activity of human blood from cancer patients.
Figure 4:
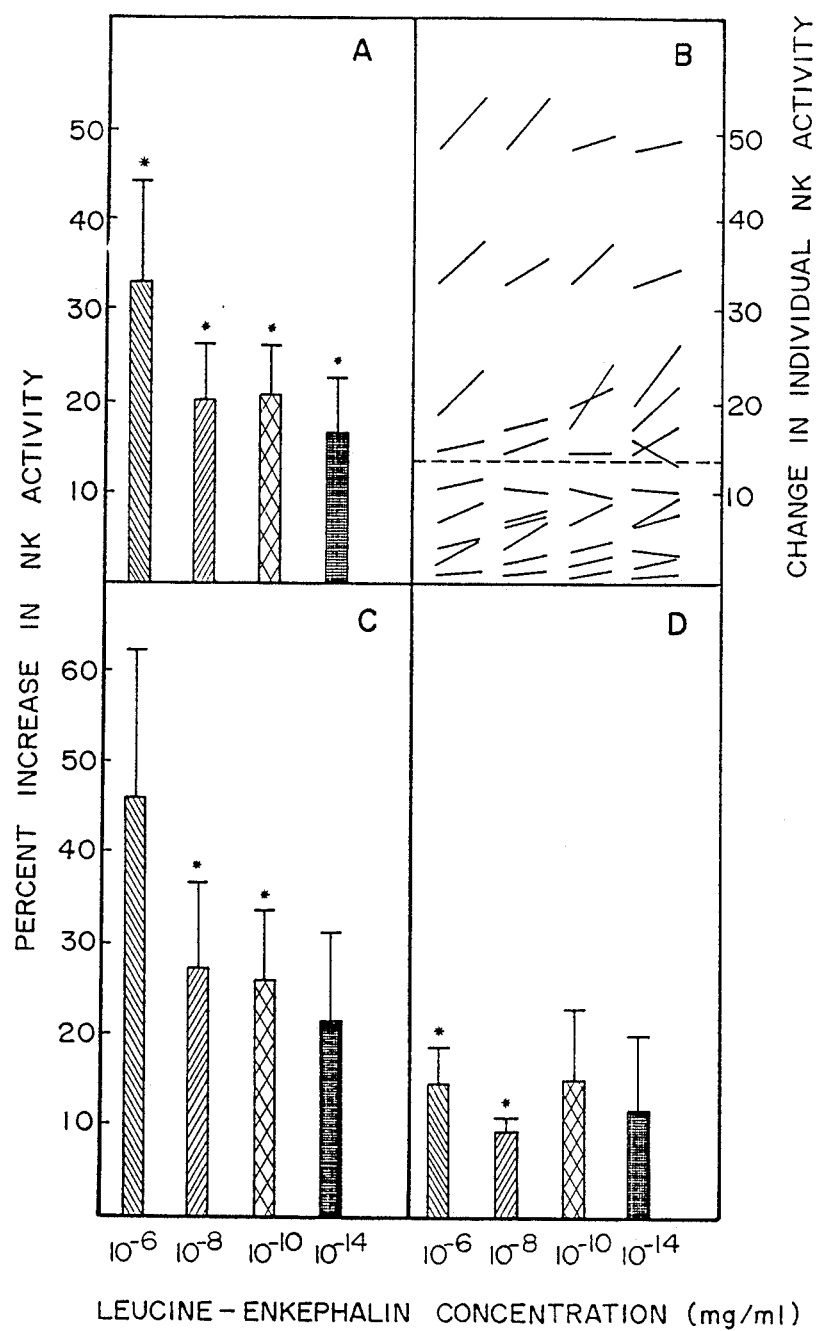
FIG. 4 illustrates the in vivo effect of leucine-enkephalin on the NK cell activity of human blood from cancer patients.

As presented in TABLES XVIII and XIX and as illustrated in FIGS. 3 and 4, methionine-enkephalin as well as leucine-enkephalin enhanced NK cell activity in peripheral blood lymphocytes isolated from cancer patients in a manner analogous to the normal volunteers. Both are effective at all concentrations tested and at all effector-to-target cell ratios investigated. The biphasic dip in enhancement for methionine-enkephalin appeared at $10^{-10}$ mg/ml while a suggestion of biphasic behavior at $10^{-8}$ mg/ml for leucine-enkephalin was present. Again, the observed percentage increase in NK activity following treatment was higher in individuals with a natural low NK activity (see data of TABLE XIX and legend B of FIGS. 3 and 4), while the percentage increase in activity was significant at all concentrations for methionine-enkephalin and two concentrations for leucine-enkephalin ($10^{-8}$ and $10^{-10}$ mg/ml) in individuals with low NK activity and was significant at only one concentration ($10^{-10}$ mg/ml) for methionine-enkephalin and two concentrations ($10^{-6}$ and $10^{-8}$) for leucine-enkephalin in individuals with high NK activity.

The results of this study confirm the previous conclusion that enkephalins are immunostimulatory. Perhaps of special interest is the observation that those normal individuals with relatively low natural NK activity exhibited the largest increase in NK activity with enkephalin treatment. This is similar to the observation made with active T-cell rosettes in lymphoma patients and normal individuals. Except in contrast to normal volunteers, lymphoma patients have low numbers of T-rosette forming cells and showed the largest increase in T-cell rosettes with enkephalin treatment. Also, there are apparent differences in the potential of enkephalins in their effects on various immune functions. Leucine-enkephalin is observed to be much more active in stimulating NK activity than methionine-enkephalin.

In contrast, previous EXAMPLES with lymphocytes from normal human volunteers as well as lymphoma patients suggest that methionine-enkephalin is more active than leucine-enkephalin in enhancing active T-cell rosettes. In addition, the two enkephalins exhibited potency differences in mouse splenic lymphocyte blastogenesis induced by phytohemagglutinin. Leucine-enkephalin was active at low concentrations and inactive at higher levels while methionine-enkephalin behaved in an opposite manner. These apparent differences in activity or potency of the enkephalins again suggest major differences in affinities for cellular receptors.

In view of the data it is further proposed that the enkephalins play a role in a central nervous system-endocrine-immune interrelationship in which dysfunctions in the immune system may be chronic stress related and be accompanied by perturbations in enkephalin levels in the adrenals, the primary source of enkephalins in peripheral circulation. Large amounts of enkephalins, catecholamines and steroids are secreted simultaneously from the adrenals during stress. It is well known that the central nervous system and behavior can influence immune function. Recently behavioral states have been shown to influence cerebral spinal fluid levels of endorphins and exercise has been shown to increase plasma levels of endorphins. Exercise has also been shown to enhance human NK activity. Due to these facts and the effects of enkephalins referred to above, it is felt that the enkephalins play a central role in natural immunomodulation which is influenced by a number of factors; i.e., the enkephalins are immunomodulators.

TABLE XVIII

| Patient | Age | Sex | $R_x$ | Stage | $R_x$ Prior to Study |
|---|---|---|---|---|---|
| 1 | 59 | F | Thyroid Cancer | Advanced, IV | Adriamycin 1 month prior study |
| 2 | 48 | F | Acute Myelocytic Leukemia | Bone marrow | Induction $R_x$, with Adriamycin, Prednisone, Vincristine, ARAC |
| 3 | 73 | F | Small Cell Cancer Lung, Relapse | Extensive | VP16 1 week before study |
| 4 | 30 | F | Hogdkin's Recurrent | Stage IV | Multiple chemotherapy. MOPP ABVD. Radiation $R_x$. Last $R_x$ was 1 month prior to study using methyl GaG. |
| 5 | 49 | F | Chronic Myeologenous Leukemia | Lymphoblastic Transformation | Vincristine/Prednisone during study |
| 6 | 48 | F | Breast Cancer Stage | Stage V | On Chemotherapy 5Fu, L-pam |
| 7 | 50 | F | Ovarian Cancer | Stage III | Adriamycin, Cytoxan, Cisplatinium. |

TABLE XVIII-continued

| Patient | Age | Sex | $R_x$ | Stage | $R_x$ Prior to Study |
|---|---|---|---|---|---|
| 8 | 72 | M | Gastric Carcinoma | Advanced | 5Fu. Adriamycin, Mitomycin C, Radiation $R_x$. |
| 9 | 90 | M | Poorly differentiated, lymphocytic lymphoma, modular | IV | No chemotherapy for several months, prior to that received C-M Opp. |
| 10 | | | | | |
| 11 | 46 | F | Diffuse Histiocytic Lymphoma | III | CHOP. Radiation to abdomen. COP-BLAM. 2 weeks prior to study. |
| 12 | | | Modular Histiocytic Lymphoma | IV | CHOP-Chemotherapy 1 month prior to study. 7 courses given up to date of study. |

TABLE XIX

Effect of Enkephalin on NK Cells Activity

| | 100:1 | % ↑↓ | 33:1 | % ↑↓ | 11:1 | % ↑↓ |
|---|---|---|---|---|---|---|
| Patient 1 | | | | | | |
| Control | 23.99 | | 10.70 | | 3.61 | |
| Methionine-Enkephalin | | | | | | |
| $10^{-6}$ mg/ml | 28.80 | 20.05 ↑ | 12.96 | 21.12 ↑ | 5.26 | 45.71 ↑ |
| $10^{-8}$ | 30.50 | 27.14 ↑ | 13.20 | 23.36 ↑ | 4.70 | 30.19 ↑ |
| $10^{-10}$ | 30.39 | 26.68 ↑ | 10.79 | 0.89 ↑ | 4.28 | 18.56 ↑ |
| $10^{-14}$ | 30.76 | 29.05 ↑ | 13.28 | 24.11 ↑ | 4.41 | 22.16 ↑ |
| Leucine-Enkephalin | | | | | | |
| $10^{-6}$ | 30.40 | 26.72 ↑ | 11.55 | 7.94 ↑ | 4.41 | 22.16 ↑ |
| $10^{-8}$ | 28.37 | 18.26 ↑ | 10.29 | 3.83 ↓ | 4.44 | 22.99 ↑ |
| $10^{-10}$ | 27.11 | 13.01 ↑ | 9.79 | 8.50 ↓ | 4.26 | 18.01 ↑ |
| $10^{-14}$ | 28.32 | 18.05 ↑ | 10.34 | 3.36 ↓ | 3.73 | 3.32 ↑ |
| Patient 2 | | | | | | |
| Control | 9.52 | | 2.12 | | 0.78 | |
| Methionine-Enkephalin | | | | | | |
| $10^{-6}$ | 10.51 | 12.40 ↑ | 2.89 | 36.32 ↑ | 1.96 | 151.28 ↑ |
| $10^{-8}$ | 10.04 | 5.46 ↑ | 3.57 | 68.40 ↑ | 1.46 | 87.18 ↑ |
| $10^{-10}$ | 9.78 | 2.73 ↑ | 2.91 | 37.26 ↑ | 1.27 | 62.82 ↑ |
| $10^{-14}$ | — | — | 3.23 | 52.36 ↑ | 1.72 | 120.51 ↑ |
| Leucine-Enkephalin | | | | | | |
| $10^{-6}$ | — | — | 4.66 | 119.81 ↑ | 1.79 | 129.49 ↑ |
| $10^{-8}$ | — | — | 2.95 | 39.15 ↑ | 1.79 | 129.49 ↑ |
| $10^{-10}$ | — | — | 2.86 | 34.91 ↑ | 1.26 | 61.54 ↑ |
| $10^{-14}$ | — | — | 3.10 | 46.23 ↑ | 0.95 | 21.79 ↑ |
| Patient 3 | | | | | | |
| Control | — | | 19.95 | | 17.76 | |
| Methionine-Enkephalin | | | | | | |
| $10^{-6}$ mg/ml | — | | — | | — | |
| $10^{-8}$ | — | | — | | — | |
| $10^{-10}$ | — | | 22.33 | | 17.74 | |
| $10^{-14}$ | — | | 25.48 | | 24.01 | |
| Leucine-Enkephalin | | | | | | |
| $10^{-6}$ | — | | — | | — | |
| $10^{-8}$ | — | | — | | — | |
| $10^{-10}$ | — | | 25.28 | | 20.27 | |
| $10^{-14}$ | — | | 27.03 | | 22.74 | |
| Patient 4 | | | | | | |
| Control | | | 17.02 | | 7.62 | |
| Methionine-Enkephalin | | | | | | |
| $10^{-6}$ | — | | 18.77 | | 8.62 | |
| $10^{-8}$ | — | | 21.60 | | 9.42 | |
| $10^{-10}$ | — | | 21.97 | | 9.04 | |
| $10^{-14}$ | — | | 23.45 | | 10.09 | |
| Leucine-Enkephalin | | | | | | |
| $10^{-6}$ | — | | 23.66 | | 10.86 | |
| $10^{-8}$ | — | | 18.27 | | 10.17 | |
| $10^{-10}$ | — | | 24.56 | | 12.75 | |
| $10^{-14}$ | — | | 22.17 | | 12.06 | |
| Patient 5 | | | | | | |
| Control | 1.00 | | 0.812 | | 0.247 | |
| Methionine-Enkephalin | | | | | | |
| $10^{-6}$ mg/ml | 1.73 | | 1.19 | | 0.545 | |
| $10^{-8}$ | 1.98 | | 1.09 | | 0.693 | |
| $10^{-10}$ | 2.49 | | 1.18 | | 0.7 | |
| $10^{-14}$ | 2.53 | | 1.305 | | 0.141 | |
| Leucine-Enkephalin | | | | | | |
| $10^{-6}$ | 1.56 | | 1.28 | | 0.493 | |
| $10^{-8}$ | 2.57 | | 1.04 | | 0.765 | |
| $10^{-10}$ | 2.34 | | 1.32 | | 1.241 | |
| $10^{-14}$ | 1.68 | | 1.09 | | 0.752 | |
| Patient 6 | | | | | | |
| Control | | | 6.50 | — | 3.85 | — |
| Methionine-Enkephalin | | | | | | |
| $10^{-6}$ | | | 8.76 | 34.77 ↑ | 3.69 | 4.16 ↓ |
| $10^{-8}$ | | | 8.75 | 34.62 ↑ | 4.01 | 9.35 ↑ |
| $10^{-10}$ | | | 7.58 | 16.62 ↑ | 4.57 | 18.70 ↑ |
| $10^{-14}$ | | | 8.40 | 29.23 ↑ | 4.15 | 7.79 ↑ |
| Leucine-Enkephalin | | | | | | |
| $10^{-6}$ | | | 8.79 | 35.23 ↑ | 3.44 | 10.65 ↓ |
| $10^{-8}$ | | | 7.51 | 15.54 ↑ | 4.13 | 7.27 ↑ |
| $10^{-10}$ | | | 8.78 | 35.08 ↑ | 5.07 | 31.69 ↑ |
| $10^{-14}$ | | | 7.73 | 18.90 ↑ | 5.26 | 36.62 ↑ |
| Patient 7 | | | | | | |
| Control | | | 33.44 | — | 16.54 | — |
| Methionine-Enkephalin | | | | | | |
| $10^{-6}$ | | | 37.67 | 12.65 ↑ | 20.78 | 25.63 ↑ |
| $10^{-8}$ | | | 40.65 | 21.56 ↑ | 19.86 | 20.17 ↑ |
| $10^{-10}$ | | | 40.20 | 20.22 ↑ | 17.94 | 8.46 ↑ |
| $10^{-14}$ | | | 40.87 | 22.22 ↑ | 19.46 | 17.65 ↑ |
| Leucine-Enkephalin | | | | | | |
| $10^{-6}$ | | | 38.07 | 13.85 ↑ | 16.76 | 1.33 ↑ |
| $10^{-8}$ | | | 36.34 | 8.67 ↑ | 19.61 | 18.56 ↑ |
| $10^{-10}$ | | | 38.44 | 14.95 ↑ | 16.85 | 1.87 ↑ |
| $10^{-14}$ | | | 34.99 | 4.64 ↑ | 17.85 | 7.92 ↑ |
| Patient 8 | | | | | | |
| Control | | | 14.59 | — | 8.59 | — |
| Methionine-Enkephalin | | | | | | |
| $10^{-6}$ | | | 17.39 | 19.19 ↑ | 9.20 | 7.10 ↑ |
| $10^{-8}$ | | | 16.61 | 13.85 ↑ | 9.67 | 12.57 ↑ |
| $10^{-10}$ | | | 16.53 | 13.30 ↑ | 10.19 | 18.63 ↑ |
| $10^{-14}$ | | | 16.39 | 12.34 ↑ | 9.25 | 7.68 ↑ |
| Leucine-Enkephalin | | | | | | |
| $10^{-6}$ | | | 15.63 | 7.13 ↑ | 10.03 | 16.76 ↑ |
| $10^{-8}$ | | | 16.33 | 11.93 ↑ | 8.72 | 1.51 ↑ |
| $10^{-10}$ | | | 14.87 | 1.92 ↑ | 9.03 | 5.12 ↑ |
| $10^{-14}$ | | | 17.23 | 18.09 ↑ | 9.63 | 12.11 ↑ |
| Patient 9 | | | | | | |
| Control | | | 48.37 | | 30.25 | |
| Methionine-Enkephalin | | | | | | |
| $10^{-6}$ | | | 41.60 | | 28.20 | |
| $10^{-8}$ | | | 46.93 | | 31.58 | |
| $10^{-10}$ | | | 47.41 | | 29.72 | |

TABLE XIX-continued

Effect of Enkephalin on NK Cells Activity

| | 100:1 | % ↑↓ | 33:1 | % ↑↓ | 11:1 | % ↑↓ |
|---|---|---|---|---|---|---|
| $10^{-14}$ | | | 50.47 | | 33.15 | |
| Leucine-Enkephalin | | | | | | |
| $10^{-6}$ | | | 53.80 | | 34.58 | |
| $10^{-8}$ | | | 53.99 | | 33.67 | |
| $10^{-10}$ | | | 49.81 | | 32.74 | |
| $10^{-14}$ | | | 49.44 | | 32.69 | |
| Patient 10 | | | | | | |
| Control | 5.99 | | 3.85 | | 3.11 | |
| Methionine-Enkephalin | | | | | | |
| $10^{-6}$ | 10.07 | | 3.96 | | 1.51 | |
| $10^{-8}$ | 11.12 | | 5.53 | | 2.18 | |
| $10^{-10}$ | 13.36 | | 6.00 | | 3.14 | |
| $10^{-14}$ | 12.68 | | 4.57 | | 2.38 | |
| Leucine-Enkephalin | | | | | | |
| $10^{-6}$ | 14.32 | | 4.86 | | 2.73 | |
| $10^{-8}$ | 11.45 | | 6.32 | | 2.52 | |
| $10^{-10}$ | 12.50 | | 4.55 | | 2.72 | |
| $10^{-14}$ | 10.94 | | 3.48 | | 1.54 | |
| Patient 11 | | | | | | |
| Control | | | 16.17 | | 8.57 | |
| Methionine-Enkephalin | | | | | | |
| $10^{-6}$ | | | | | | |
| $10^{-8}$ | | | | | | |
| $10^{-10}$ | | | | | | |
| $10^{-14}$ | | | 14.99 | | 8.93 | |
| Leucine-Enkephalin | | | | | | |
| $10^{-6}$ | | | | | | |
| $10^{-8}$ | | | | | | |
| $10^{-10}$ | | | | | | |
| $10^{-14}$ | | | 13.05 | | 9.08 | |
| Patient 12 | | | | | | |
| Control | 12.47 | — | 6.71 | — | 3.37 | — |
| Metionine-Enkephalin | | | | | | |
| $10^{-6}$ | 13. | 6.20 ↑ | 6.84 | 1.94 ↑ | 3.73 | 16.62 ↑ |
| $10^{-8}$ | 13.27 | 11.23 ↑ | 7.19 | 7.15 ↑ | 4.20 | 24.63 ↑ |
| $10^{-10}$ | 13.66 | 9.54 ↑ | 6.77 | 3.87 ↑ | 4.34 | 28.78 ↑ |
| $10^{-14}$ | 14.36 | 15.11 ↑ | 7.73 | 15.2 ↑ | 4.23 | 25.52 ↑ |
| Leucine-Enkephalin | | | | | | |
| $10^{-6}$ | 15.02 | 20.45 ↑ | 8.60 | 28.17 | 4.44 | 31.75 ↑ |
| $10^{-8}$ | 14.50 | 16.28 ↑ | 7.94 | 18.33 | 4.27 | 26.71 ↑ |
| $10^{-10}$ | 16.06 | 28.79 ↑ | 8.59 | 28.02 | 4.75 | 46.88 ↑ |
| $10^{-14}$ | 14.72 | 18.04 ↑ | 9.49 | 41.43 | 5.58 | 65.58 ↑ |

In order to demonstrate, in vivo, the highly positive stimulatory effects of methionine-enkephalin on T cells and NK cells when infused directly into the blood stream, clinical testing on normal human volunteers was performed using methods of analysis analogous to the previous EXAMPLES. All prospective volunteers were screened and found to be normal in physical examination as well as clinical laboratory analysis. No candidates were admitted to the study with any medical history and candidates were particularly screened to be allergy free. The screened volunteers were admitted to the hospital the evening before the study. The next morning intravenous infusion of methionine-enkephalin was started at 9:00 a.m. for 30 minutes. Blood examples and vital signs were taken at appropriate intervals. The following examples summarize the results of the respective volunteers.

EXAMPLE VIII

The first volunteer received 10 micrograms/kg of methionine-enkephalin per kilogram of body weight. The level of active T-cell rosette cells increased 183% at 2 hours after infusion and 103% after 24 hours. The level of total T-cell rosettes also increased 98% at 2 hours and 82% at 24 hours over baseline control levels. In contrast, the NK cell levels were found to be reduced 24% at 2 hours and 56% at 24 hours after infusion (characteristic of normal volunteers at high control levels). No significant changes were seen in the blood pressure, temperature or EKG. Slight increase in heart rate and respiration were recorded. Neurological evaluations indicated slight nystagmus 1 to 2 hours after infusion. The 100 mm line test for behavioral effects indicated a shift in the score to the "happy" side for the rest of the study. The following TABLES XX through XXIV summarize the results of Volunteer No. 1.

TABLE XX

Methionine-Enkephalin (0.010 mg/kg)

| | Blood Pressure | | Heart Rate | Resp. Rate | Temp. |
|---|---|---|---|---|---|
| First Day | | S/E | | | |
| 8 a.m. | 100/70 | 100/70 | 44/45 | 12 | 98 F. |
| 8:55 | 100/70 | 100/70 | 50/52 | 13 | 98.8 |
| 9:00 | METHIONINE-ENKEPHALIN INFUSION | | | | |
| 9:10 | 100/70 | | 60 | 14 | 98.8 |
| 9:20 | 100/70 | | 60 | 12 | 98.8 |
| 9:30 | 100/70 | | 60 | 12 | 98.8 |
| 10 a.m. | 110/70 | | 64 | 12 | 98.8 |
| 11 a.m. | 100/70 | | 60 | 14 | 98.6 |
| 1 p.m. | 100/70 | 100/70 | 45/60 | 12 | 98.4 |
| 4 p.m. | 100/70 | 100/70 | 44/56 | 13 | 98.4 |
| Second Day | | | | | |
| 8:55 | 100/70 | 100/70 | 45/60 | 12 | 98.4 |

TABLE XXI 100 mm. LINE TEST
DOSE - 10 micrograms per kg.

| First Day | 8:30 a.m. | 55.0 mm. |
|---|---|---|
| | 8:55 a.m. | 59.0 mm. |
| | 9:30 a.m. | 55.0 mm. |
| | 10:00 a.m.* | 38.0 mm. |
| | 11:00 a.m.* | 38.0 mm. |
| | 1:00 p.m.* | 43.0 mm. |
| | 4:00 p.m.* | 40.0 mm. |
| Next Day | 8:55 a.m. | 39.0 mm. |

TABLE XXII

Methionine-Enkephalin (0.01 mg/kg)
Active T-Cell Rosettes
MEAN VALUE

| CONTROLS | 30/200 | |
|---|---|---|
| 2 hours | 85/200 | 183% INCREASE* |
| 24 hours | 61/200 | 103% INCREASE* |

TABLE XXIII

Methionine-Enkephalin (0.01 mg/kg)
Total T-Cell Rosettes
MEAN VALUE

| CONTROLS | 62/200 | |
|---|---|---|
| 2 hours | 123/200 | 98% INCREASE* |
| 24 hours | 113/200 | 82% INCREASE* |

TABLE XXIV

NK Cell Activity
Methionine-Enkephalin (0.01 mg/kg)
RATIO 33:1

| | % ACTIVITY | |
|---|---|---|
| CONTROLS | 51% | |
| 2 HOURS | 39% | 24% DECREASE |

TABLE XXIV-continued

NK Cell Activity
Methionine-Enkephalin (0.01 mg/kg)
RATIO 33:1

| | % ACTIVITY | |
|---|---|---|
| 24 HOURS | 23% | 56% DECREASE |

EXAMPLE IX

In a manner analogous to Volunteer No. 1 of EXAMPLE VIII, Volunteer No. 2 received 10 micrograms of methionine-enkephalin per kilogram of body weight. The volunteer showed significant increases of active T-cell rosettes of 126% in 2 hours and 26% at 24 hours after infushion. Only slight increases were seen in the total T-cell rosettes. The NK cell levels showed a slight decrease (10% at 2 hours) but a highly significant increase at 33% at 24 hours. No changes were seen in blood pressure, body temperature, or EKG. Slight decreases in heart rate were seen in the afternoon following the infusion. Neurological evaluation indicated a slight nystagmus 2 hours after infusion. And again, a slight shift towards the "happy" side was seen in the 100 millimeter line test score. The following TABLES XXV-XXX summarize the results of in vivo testing of Volunteer No. 2.

TABLE XXV

Methionine-Enkephalin (0.010 mg/kg)

| | Blood Pressure | | Heart Rate S/E | Resp. Rate | Temp. |
|---|---|---|---|---|---|
| First Day | | | | | |
| 8 a.m. | 130/80 | 130/80 | 72/80 | 12 | 98 F. |
| 8:55 | 130/80 | 130/87 | 70/76 | 12 | 98 |
| 9:00 | Methionine-Enkephalin Infusion | | | | |
| 9:10 | 130/80 | | 70 | 10 | 98 |
| 9:20 | 130/80 | | 62 | 12 | 98 |
| 9:30 | 130/80 | | 72 | 12 | 98 |
| 10:00 | 130/80 | | 76 | 12 | 98 |
| 11:00 | 130/80 | 130/80 | 66/70 | 13 | 98 |
| 1 p.m. | 130/80 | 130/80 | 64/70 | 13 | 98 |
| 4 p.m. | 130/80 | 140/80 | 68/72 | 12 | 98 |
| Next Day | | | | | |
| 8:44 | 130/80 | 130/80 | 64/72 | 12 | 98 |

TABLE XXVI 100 mm. Line Test
DOSE = 10 micrograms per kg.

| First Day | |
|---|---|
| 8:00 a.m. | 49.0 mm. |
| 8:55 a.m. | 46.0 mm. |
| 9:30 a.m.* | 44.0 mm. |
| 10:00 a.m. | 47.0 mm. |
| 11:00 a.m. | 50.0 mm. |
| 1:00 p.m. | 49.0 mm. |
| 4:00 p.m. | 50.0 mm. |
| Next Day | |
| 8:55 a.m.* | 44.0 mm. |

TABLE XXVII

Methionine-Enkephalin (0.01 mg/kg)
Active T-Cell Rosettes
MEAN VALUE

| CONTROLS | 34/200 | |
|---|---|---|
| 2 hours | 77/200 | 126% Increase |
| 24 hours | 43/200 | 26% Increase |

TABLE XXVIII

Methionine-Enkephalin (0.01 mg/kg)
Total T-Cell Rosettes
MEAN VALUE

| CONTROLS | 113/20 | |
|---|---|---|
| 2 hours | 117/200 | 4% Increase |
| 24 hours | 123/200 | 9% Increase |

TABLE XXIX

NK CELLS
11:1 RATIO
Methionine-Enkephalin (0.010 mg/kg)

| CONTROLS - 19% | |
|---|---|
| 2 hours - 17% | 10% Decrease |
| 24 hours - 25%* | 33% Increase |

TABLE XXX

Methionine-Enkephalin (0.01 mg/kg)
NK CELL ACTIVITY

| | RATIO 33:1 % ACTIVITY | | RATIO 11:1 % ACTIVITY | |
|---|---|---|---|---|
| CONTROLS | 38% | | 19% | |
| 2 hours | 36% | 6% Decrease | 17% | 10% Decrease |
| 24 hours | 32% | 16% Decrease | 25% | 33% Increase |

EXAMPLE X

In view of the composite of the results associated with Volunteer No. 1 and No. 2, a third volunteer was administered a smaller dose of methionine-enkephalin (0.001 mg/kg) corresponding closer to the original in vitro test concentrations of methionine-enkephalin. Significant increases in active T-cell rosettes were seen at 2 and 24 hours of 71% and 53%, respectively, over control levels. Essentially no change in total T-cell rosettes was observed. Significant increases (15% and 30%) in the level of NK cells were seen at 2 and 24 hours after infusion of the methionine-enkephalin. Slight decreases in heart rate and respiratory rate were recorded at the end of the infusion. No other significant changes were detected. Slight nystagmus as well as a slight shift on the 100 millimeter line test to the "happy" side was recorded following the infusion. The following TABLES XXXI through XXXVI summarize the results of Volunteer No. 3.

TABLE XXXI

Methionine-Enkephalin (0.001 mg/kg)

| | Blood Pressure | | Heart Rate S/E | Resp. Rate | Temp. |
|---|---|---|---|---|---|
| First Day | | | | | |
| 8 a.m. | 110/80 | 110/80 | 52/60 | 12 | 98° F. |
| 8:30 | 110/80 | 110/80 | 56/60 | 12 | 98 |
| 8:55 | 110/80 | 110/80 | 52/60 | 12 | 98 |
| 9:00 | Methionine-Enkephalin Infusion | | | | |
| 9:10 | 110/80 | | 55 | 12 | 98 |
| 9:20 | 110/80 | | 55 | 12 | 98 |
| 9:30 | 110/80 | | 50 | 12 | 98 |

TABLE XXXI-continued

Methionine-Enkephalin (0.001 mg/kg)

| | Blood Pressure | Heart Rate S/E | Resp. Rate | Temp. |
|---|---|---|---|---|
| 10:00 | 110/80 | 54 | 10 | 98 |
| 11:00 | 110/80 | 120/80 56/62 | 12 | 98 |
| 1 p.m. | 110/80 | 110/80 55/58 | 12 | 98 |
| 4 p.m. | 110/80 | 110/80 55/58 | 12 | 98 |
| Next Day | | | | |
| 8:55 | 110/80 | 120/80 54/60 | 12 | 98 |

TABLE XXXII 100 mm. LINE TEST
DOSE = one microgram per kg.

| 8:00 a.m. | 23.0 mm. |
|---|---|
| 8:30 a.m. | 39.0 mm. |
| 8:55 a.m. | 37.0 mm. |
| 9:30 a.m. | 41.0 mm. |
| 10:00 a.m.* | 28.0 mm. |
| 11:00 a.m.* | 36.0 mm. |
| 1:00 p.m. | 35.0 mm. |
| 4:00 p.m. | 39.0 mm. |

TABLE XXXIII

Methionine-Enkephalin (0.001 mg/kg)
Active T-cell Rosettes
MEAN VALUE

| CONTROLS | 17/200 | |
|---|---|---|
| 2 hours | 29/200 | 71% Increase |
| 24 hours | 26/200 | 53% Increase |

TABLE XXXIV

Methionine-Enkephalin (0.001 mg/kg)
Total T-Cell Rosettes
MEAN VALUE

| CONTROLS | 100/200 | |
|---|---|---|
| 2 hours | 106/200 | 6% Increase |
| 24 hours | 108/200 | 8% Increase |

TABLE XXXV

Methionine-Enkephalin (0.001 mg/kg)
NK Cell Activity (33:1)
% Activity

| CONTROLS | 39% | |
|---|---|---|
| 2 hours | 36% | 8% Decrease |
| 24 hours | 50% | 28% Increase |

TABLE XXXVI

Methionine-Enkephalin (0.001 mg/kg)
11:1 RATIO

| CONTROLS | 20% | |
|---|---|---|
| 2 hours | 24% | 15% Increase |
| 24 hours | 27% | 30% Increase |

EXAMPLE XI

In a manner analogous to Volunteer No. 3 of EXAMPLE IV, Volunteer No. 4 received 0.001 mg/kg of methionine-enkephalin. Volunteer No. 4 showed a significant increase of active T-cell rosettes of 148% in 2 hours and a decrease of 45% after 24 hours from infusion. Again, no significant change in total T-cell rosettes took place. Analogous to Volunteer No. 1 of EXAMPLE VIII, the NK cell levels were found to be reduced 30% at 2 hours and 34% at 24 hours relative to a high control level of a healthy normal volunteer. All other measurements and values were essentially equivalent to the previous volunteers as exhibited in the following TABLES XXVII through XXXVII.

TABLE XXXVII

DOSE = one microgram per kg.

| | Blood Pressure | Heart Rate | Resp. Rate | Temp. |
|---|---|---|---|---|
| First Day | | | | |
| 8:00 a.m. | 110/80 | 110/80 60/64 | 12/min. | 98.2° F. |
| 8:55 | 110/80 | 110/80 60/64 | 12 | 98.1 |
| 9:00 | | Methionine-Enkephalin Infusion | | |
| 9:10 | 110/80 | 63 | 13 | 98.2 |
| 9:20 | 100/80 | 67 | 12 | 98.2 |
| 9:30 | 100/80 | 57 | 12 | 98.2 |
| 10:00 | 110/80 | 74 | 10 | 98.2 |
| 11:00 | 100/80 | 100/80 66 | 12 | 98 |
| 1:00 p.m. | 110/70 | 110/70 60/64 | 11 | 98 |
| 4:00 | 110/70 | 110/70 58/62 | 12 | 98 |
| Next Day | | | | |
| 8:55 a.m. | 120/80 | 120/80 75/78 | 12 | 97 |

TABLE XXVIII 100 mm. Line Test
Dose = one microgram per kg.

| First Day | 7:30 a.m. | 26.0 mm. |
|---|---|---|
| | 8:30 | 45.0 mm. |
| | 8:55 | 29.0 mm. |
| | 10:00° | 26.0 mm. |
| | 11:00 | 32.0 mm. |
| | 1:00 p.m. | 32.0 mm. |
| | 4:00 | 38.0 mm. |
| Second Day | 8:55 a.m. | 29.0 mm. |

TABLE XXXIX

Methionine-Enkephalin (0.001 mg/kg)
T-cell Rosettes
MEAN VALUE

| Controls | 31/200 | |
|---|---|---|
| 2 hours | 77/200 | 148% Increase |
| 24 hours | 17/200 | 45% Decrease |

TABLE XL

Methionine-Enkephalin (0.001 mg/kg)
Total T-Cell Rosettes
MEAN VALUE

| Controls | 116/200 | |
|---|---|---|
| 2 hours | 124/200 | 4% Increase |
| 24 hours | 110/200 | 3% Decrease |

TABLE XLI

Methionine-Enkephalin (0.001 mg/kg)
NK Cell Activity

| | 100:1 | |
|---|---|---|
| Controls | 59% | |
| 2 hours | 49% | 17% Decrease |
| 24 hours | 44% | 25% Decrease |
| | 33:1 | |
| Controls | 31% | |
| 2 hours | 22% | 30% Decrease |
| 24 hours | 21% | 34% Decrease |

EXAMPLE XII

In a manner analogous to the previous volunteers, Volunteers No. 5 and 6 were administered dosages of 50 micrograms of methionine-enkephalin per kilogram of body weight. The resulting active T-cell rosettes, total T-cell rosettes, and NK cell analysis at effector-to-target ratios are presented in TABLES XIII through XLII.

TABLE XLII

Dose = Fifty Micrograms/kg.
Active T-cell Rosettes

|          | No. 5 | No. 6 |
|----------|-------|-------|
| Controls | 17%   | 3%    |
| 2 hours  | 41%   | 7%    |
| 24 hours | 8%    | 22%   |

TABLE XLIII

Dose = Fifty Micrograms/kg
Total T-Cell Rosettes

|          | #5  | #6  |
|----------|-----|-----|
| Controls | 48% | 59% |
| 2 hours  | 64% | 63% |
| 24 hours | 59% | 65% |

TABLE XLIV

NK Cells 33:1

|          | #5 |       | #6 |        |
|----------|----|-------|----|--------|
| Controls | 35 |       | 16 |        |
| 2 hours  | 56 | 69% ↑ | 19 | 18 ↑   |
| 24 hours | 40 | 5% ↑  | 33 | 106 ↑  |

TABLE XLV

NK Cells 11:1

|          | #5 |       | #6  |        |
|----------|----|-------|-----|--------|
| Controls | 18 |       | 7%  |        |
| 2 hours  | 30 | 66% ↑ | 7%  |        |
| 24 hours | 17 | 5% ↓  | 16% | 129% ↑ |

EXAMPLE XIII

In order to evaluate and demonstrate the efficacy of the therapeutic treatment according to the present invention, an AIDS patient was treated on an experimental basis in compliance with the FDA. This patient was diagnosed as an AIDS patient on the basis of defective T helper cell levels compared to T suppressor cell levels consistent with the earlier studies by Ciobanu et al, Defective T-Cell Response to PHA and Mitogenic Monoclonal Antibodies in Male Homosexuals with Acquired Immunodeficiency Syndrome and Its in Vitro Correction by Interleukin 2, J. Clin. Immun. 3, 4, 1983, wherein AIDS is defined as a proliferative T-cell defect with defective interleukin 2 production and increased in percentage of suppressor cytotoxic T-cell subpopulations compared to T helper cells.

Upon admission to the hospital, this AIDS patient was suffering from swollen lymph nodes, fever, Kaposis sarcoma, and suspected Pneumocystis. Initially, the patient was placed on pentamidine therapy for suspected pneumocystistic carinii pneumonia. After the initial treatment with pentamidine, the patient was placed on methionine-enkephalin treatment. At this point, the disease had progressed to such an extent that it was this hospital's experience that this patient was terminal.

Initially, the AIDS patient was treated with daily i.v. injections of methionine-enkephalin. The daily injections continued for five days and then were restricted back to twice a week. The dose employed during the first week (5 days) was 10 micrograms per kg prepared in a normal saline solution and was infused over a 30 minute period. During the second week and for a total of two additional weeks, the patient was placed on a maintenance dosage of 25 micrograms per kg twice weekly. Twenty-four hours after each infusion or prior to the next infusion, blood samples were withdrawn and analyzed for T-cell functions, including active T-cells (sheep red blood cell rosetting) OKT 3 T-lymphocytes, mature thymocytes, OKT 11 T-lymphocytes-early development stage thymocytes, T helper cells (OKT 4), T suppressor cells (OKT 8), blastogenesis or lymphocyte proliferation, phythohemagglutinin (T helper cell mitogen), concanavalin A (T-helper and T suppressor cell mitogen), pokeweed (T dependent B cell mitogen), and Staph A (B cell mitogen). The NK cell assay (natural killer cells) was conducted against the K-562 tumor cell line labeled with $^{51}$Cr.

As indicated in Table XLVI, during the first week of treatment Monday through Friday (5 days), the T helper cell popula tion, OKT 4, increased in number from 57 to 94/mm$^3$ and the T suppressor cell population, OKT 8, decreased from 382 to 264/mm$^3$ which can be literally interpreted as therapeutic relative to the previous definition of AIDS. There was a slight increase in OKT 3 and OKT 11 cells. The T helper/T suppressor ratio rose from 0.149 to 0.354. The total lymphocytes dropped from 516 on Monday to 368 on Thursday and rose again to 550 on Friday. Active T-cells (rosettes SRBC) rose significantly from 201 on Monday to 396/mm$^3$ on Friday.

No methionine-enkephalin was infused on Saturday or Sunday, Monday morning (day 8), blood samples were withdrawn followed by methionine-enkephalin infusion (dose of 25 micrograms/Kg corresponding to one-half of the first week total dose). The T-cells were still elevated on Monday a.m. compared to Friday a.m.; OKT 4 was 110 compared to 94, OKT 8 increased to 409 from 264, OKT 3 increased from 341 to 491/mm$^3$ and OKT 11 increased from 429 on Friday to 558 on Monday. The active T cells increased to 565 on Monday compared to 396/mm$^3$ on Friday. Furthermore, the total lymphocytes increased to 774 on Monday compared to 550/mm$^3$ on Friday. The NK cell assay on Monday of the second week was slightly decreased compared to the Monday levels of the first week.

On Thursday of the second week (day 11), blood samples were taken once again followed by the methionine-enkephalin infusion. All of the T-cells subsets increased except active T-cells (rosettes). Lymphocyte count diminished slightly.

The patient was discharged from the hospital with signs of subjective improvement. The original lesions associated with the sarcoma (on the right side of the body) including biopsy hole was crusting and healing. Lymph nodes in the axillary area and groin were palpably smaller.

The data of this Example further supports and correlates well with the previous in vivo and in vitro data, particularly in the methionine-enkephalin stimulates PHA-induced blastogenesis (a T helper cell antigen) in mice and also markedly stimulates OKT 4 (T helper cell) production in normal volunteers. Similar elevations of T helper cells by met-enkephalin are observed in the present AIDS patient with kaposis sarcoma. In addition, there was a marked elevation of interleukin 2 receptors to 48 percent of the lymphocytes compared to 14 percent on day 1. Blastogenesis to the PHA stimulation (day 8) was markedly increased. Also, con A, pokeweed, and Staph A were increased slightly.

Therapeutic treatment of the AIDS patient on an outpatient basis has continued. In addition to the early observation that the two skin lesions associated with the kaposis sarcoma regressed, but the bad lesion in the gums progressed, subjective improvement in the oral lesion has now been observed. Furthermore, the AIDS patient has not demonstrated any episode of infection since the initiation of the therapeutic treatment, a phenomenon not characteristic of AIDS. In view of the above, it is felt that the therapeutic efficacy of the process according to the present invention has been verified and, in fact, has sustained life free of infection in a manner previously unknown in the art. Specifically, the above Example illustrates that methionine-enkephalin is useful as a therapy for prevention of infections associated with bacterial, viral, fungal diseases; cancers, parasites, chemotherapy, radiation and surgery.

ously resisted all therapeutic treatment was administered a sequence of methionine-enkephalin i.v. infusions. The treatment regimen, dosage and analysis scheme was essentially identical to the AIDS patient; however, in this case, the lung cancer patient's initial immune system parameters were not catastrophically depressed prior to treatment. Results of the methionine-enkephalin treatment are presented in Table XLVII.

As indicated by the data, the lung cancer patient upon methionine-enkephalin treatment showed a significant increase in T-cell subsets, including active T-cell rosettes, OKT 3, OKT 4-helper cells, and OKT 8 resulting in an increase in interleukin 2 receptors to 60 percent. There was also a major increase in lymphocyte count. Concurrent with this immune system stimulation, a subjective improvement in the well being of the patient was observed, particularly with respect to a lack of infections during the last seven weeks. Thus, again, the therapeutic utility of the treatment according to the present invention with respect to the suppression and inhibition of infection was confirmed.

TABLE XLVI

| ASSAYS | DAYS | | | | | | | | | | | | | | |
|---|---|---|---|---|---|---|---|---|---|---|---|---|---|---|---|
| | 1 | 2 | 3 | 4 | 5 | 8 | 11 | 15 | 18 | 22 | 26 | 29 | 32 | 36 | 38 |
| Active T cells | | | | | | | | | | | | | | | |
| Percent (%) | 39 | 83 | 79 | 72 | 72 | 76 | 26 | 55 | 38 | 53 | 48 | 45 | 51 | 69 | 68 |
| Absolute (/mm$^3$) | 201 | 367 | 309 | 265 | 396 | 565 | 192 | 315 | 330 | 413 | 340 | 158 | 457 | 550 | |
| T LYMPHOCYTES & SUBSETS | | | | | | | | | | | | | | | |
| T Lymphocytes (OKT 3) | | | | | | | | | | | | | | | |
| Percent (%) | 60 | 80 | 82 | 82 | 62 | 66 | 76 | 77 | 75 | 70 | 72 | 78 | 82 | 75 | 68 |
| Absolute (/mm$^3$) | 310 | 354 | 321 | 302 | 341 | 491 | 561 | 440 | 654 | 546 | 510 | 275 | 734 | 924 | |
| T Lymphocytes (OKT 11) | | | | | | | | | | | | | | | |
| Percent (%) | 79 | 88 | 80 | 80 | 78 | 75 | 81 | 74 | 79 | 79 | 79 | 79 | 80 | 72 | 77 |
| Absolute (/mm$^3$) | 408 | 389 | 313 | 294 | 429 | 558 | 598 | 420 | 687 | 616 | 559 | 278 | 717 | 887 | |
| T helper cells (OKT 4) | | | | | | | | | | | | | | | |
| Percent (%) | 11 | 13 | 14 | 17 | 17 | 16 | 17 | 9 | 9 | 10 | 9 | 12 | 11 | 18 | 21 |
| Absolute (/mm$^3$) | 57 | 58 | 55 | 63 | 94 | 119 | 125 | 51 | 78 | 78 | 64 | 42 | 99 | 222 | |
| T suppressor cells (OKT 8) | | | | | | | | | | | | | | | |
| Percent (%) | 74 | 63 | 53 | 53 | 48 | 55 | 61 | 70 | 73 | 68 | 72 | 66 | 64 | 62 | 62 |
| Absolute (/mm$^3$) | 382 | 278 | 207 | 195 | 264 | 409 | 450 | 400 | 634 | 530 | 510 | 232 | 573 | 764 | |
| T helper/T suppressor ratio | 0.149 | 0.209 | 0.264 | 0.321 | 0.354 | 0.291 | 0.278 | 0.1275 | 0.123 | 0.1472 | 0.1255 | 0.1810 | 0.173 | 0.291 | |
| BLASTOGENESIS | | | | | | | | | | | | | | | |
| Phytohemagglutinin | 20X | — | — | — | — | 134X | — | 180X | — | 143X | | | | | |
| Concanavalin A | 11X | — | — | — | — | 49X | — | 93X | — | 52X | | | | | |
| Pokeweed | 12X | — | — | — | — | 18X | — | 43X | — | 9X | | | | | |
| Staph A | 1X | — | — | — | — | 3X | — | 18X | — | 39X | | | | | |
| Interleukin-2 Receptor (%) | 14 | — | — | — | — | 48 | — | 32 | — | 40 | | | | | |
| NK cell Assay (%) | | | | | | | | | | | | | | | |
| 100:1 | 26 | — | — | — | — | 16 | — | 15 | — | — | — | 16 | | | |
| 33:1 | 11 | — | — | — | — | 8 | — | 4 | — | — | — | 2 | | | |
| 11:1 | 5 | — | — | — | — | 3 | — | 0 | — | — | — | 0 | | | |
| Slope of killing | 0.237 | | | | | 0.156 | | 0.166 | | | | | | | |
| Lymphocytes (/mm$^3$) | 516 | 442 | 391 | 368 | 550 | 774 | 738 | 572 | 869 | 780 | 708 | 352 | 896 | 1232 | |

EXAMPLE XIV

In a manner analogous to Example XIII above, a patient suffering from lung cancer which had previ-

TABLE XLVII

| ASSAYS | DAYS | | | | | | |
|---|---|---|---|---|---|---|---|
| | 1 | 2 | 3 | 4 | 5 | 8 | 11 |
| Active T cells | | | | | | | |
| Percent | 52% | 54% | 34% | 43% | 23% | 58% | 30% |
| Absolute | 707/mm$^3$ | 587/mm$^3$ | 664/mm$^3$ | 639/mm$^3$ | 460/mm$^3$ | 1183/mm$^3$ | 572/mm$^3$ |
| T LYMPHOCYTES & SUBSETS | | | | | | | |
| T Lymphocytes (OKT 3) | | | | | | | |
| Percent | 64% | | | | | 47% | |
| Absolute | 870/mm$^3$ | | | | | 959/mm$^3$ | |
| T Lymphocytes (OKT 11) | | | | | | | |
| Percent | 77% | | | | | 50% | |
| Absolute | 1047/mm$^3$ | | | | | 1020/mm$^3$ | |

TABLE XLVII-continued

| | | | | | | | |
|---|---|---|---|---|---|---|---|
| T Helper cells (OKT 4) | | | | | | | |
| Percent | 36% | | | | | 28% | |
| Absolute | 489/mm³ | | | | | 571/mm³ | |
| T Suppressor cells (OKT 8) | | | | | | | |
| Percent | 20% | | | | | 17% | |
| Absolute | 272/mm³ | | | | | 347/mm³ | |
| T Helper/T suppressor Ratio | 1.80 | | | | | 1.65 | |
| BLASTOGENESIS | | | | | | | |
| Phytohemagglutinin | 723X | | | | | 432X | |
| Concanavalin A | 704X | | | | | 576X | |
| Pokeweed | 83X | | | | | 78X | |
| Staph A | 21X | | | | | 84X | |
| Interleukin-2 Receptor | 52% | | | | | 60% | |
| NK Cell Assay | | | | | | | |
| 100:1 | 50% | | | | | 28% | |
| 33:1 | 23% | | | | | 11% | |
| 11:1 | 11% | | | | | 6% | |
| Slope | .4369 | | | | | .2515 | |
| Lymphocytes | 1360/mm³ | 1088/mm³ | 1952/mm³ | 1488/mm³ | 2002/mm³ | 2040/mm³ | 1908/mm³ |

| | DAYS | | | | | | |
|---|---|---|---|---|---|---|---|
| ASSAYS | 15 | 18 | 22 | 25 | 29 | 32 | 36 |
| Active T cells | | | | | | | |
| Percent | 40% | 16% | 36% | 74% | 40% | 23% | 52% |
| Absolute | 686/mm³ | 316/mm³ | 685/mm³ | ND | 732/mm³ | 727/mm³ | 755/mm³ |
| T LYMPHOCYTES & SUBSETS | | | | | | | |
| T Lymphocytes (OKT 3) | | | | | | | |
| Percent | | | | | 67% | | |
| Absolute | | | | | 985/mm³ | | |
| T Lymphocytes (OKT 11) | | | | | | | |
| Percent | | | | | 74% | | |
| Absolute | | | | | 1088/mm³ | | |
| T Helper cells (OKT 4) | | | | | | | |
| Percent | | | | | 44% | | |
| Absolute | | | | | 647/mm³ | | |
| T Suppressor cells (OKT 8) | | | | | | | |
| Percent | | | | | 22% | | |
| Absolute | | | | | 323/mm³ | | |
| T Helper/T suppressor Ratio | | | | | 2.00 | | |
| BLASTOGENESIS | | | | | | | |
| Phytohemagglutinin | | | | | 864X | | |
| Concanavalin A | | | | | 711X | | |
| Pokeweed | | | | | 73X | | |
| Staph A | | | | | 44X | | |
| Interleukin-2 Receptor | | | | | 80% | | |
| NK Cell Assay | | | | | | | |
| 100:1 | | | | | 30.6% | | |
| 33:1 | | | | | 19.3% | | |
| 11:1 | | | | | 8.8% | | |
| Slope | | | | | .227 | | |
| Lymphocytes | 176/mm³ | 1974/mm³ | 1904/mm³ | ND | 1830/mm³ | 3159/mm³ | 1452 |

In view of the results of the human in vivo studies, it is again concluded and demonstrated that the enkephalins play a role as immunostimulatory agents; and when directly administered to humans, act to immunomodulate and stimulate the immune system. It is further confirmed that this immunomodulation and stimulation is broadly directed to cell-mediated immunities including active T cell and NK cell populations, and as such the administration of the enkephalins and related composition according to the present invention have activity in regulating viruses, bacteria, fungi, tumorous cells and parasites and generally all immune deficiencies including deficiencies associated with aging. It is further felt that the enkephalins and endorphins, like interferons and interleukins, are the regulators (activators of other lymphokines) which act in concert in moderating and stimulating the immune system. It is proposed but not relied upon for purposes of this invention; therefore, the present invention is not limited thereby, that enkephalins activate T cells to release interleukin 2 which in turn activates the release of interferons and interleukin 1 and 3, thus promoting a cascade of immunological effects.

Since Blalock et al, Proc. Natl. Acad. Sci. 77 10, 5972 (1980), reported antigenic and structural similarities among leukocyte interferon, ACTH, and gamma-endorphin, it can be implied that leukocyte interferon may be a precursor or is derived from a common precursor to these hormones. Furthermore, Laidow et al observed that both methionine-enkephalin and leucine-enkephalin as well as beta-endorphin inhibit phenylalanyl-t RNA synthetase, J.B.C. 255 4, 11908 (1980). The anti-tumor mechanisms of action of the enkephalins may be mediated through the immune systems by (1) T-cell lymphocytes, (2) interferons, interleukins, and (3) inhibition of phenylalanyl-t RNA synthetase. And more important, the same logic leads one to conclude that the observed significant protective effects of methionine-enkephalin and the anti-tumor activity of leucine-enkephalin of the present invention would be expected from their corresponding "precursor" molecules (e.g., beta-endorphin and dynorphin pro hormone) and molecules of similar structure derived from a common precursor. Further support for this statement can be found in and is implicit in the very present of literature references indicating that "precursor" molecules bind to receptor sites of leukocytes (lymphocytes): Hazum et l, Science, 205, 7, 1033–1935 (1980). Thus for purposes of this invention, the following closely related enkephalins and endorphins are to be considered equivalent:

TABLE XLVI

| | Peptide Structures |
|---|---|
| Met—enkephalin | Tyr—Gly—Gly—Phe—Met |
| Leu—enkephalin | Tyr—Gly—Gly—Phe—Leu |
| [Arg$^6$]—Leu—enkephalin | Tyr—Gly—Gly—Phe—Leu—Arg |
| [Arg$^6$]—Met—enkephalin | Tyr—Gly—Gly—Phe—Met—Arg |
| [Lys$^6$]—Met—enkephalin | Tyr—Gly—Gly—Phe—Met—Lys |
| [Arg$^6$—Arg$^7$]—Met—enkephalin | Tyr—Gly—Gly—Phe—Met—Arg—Arg |
| [Arg$^6$—Phe$^7$]—Met—enkephalin | Tyr—Gly—Gly—Phe—Met—Arg—Phe |
| [Arg$^6$—Gly$^7$—Leu$^8$]—Met—enkephalin | Tyr—Gly—Gly—Phe—Met—Arg—Gly—Leu |
| Alpha-Neo—endorphin | Tyr—Gly—Gly—Phe—Leu—Arg—Lys—Tyr—Pro—Lys |
| Beta-Neo—endorphin | Tyr—Gly—Gly—Phe—Leu—Arg—Lys—Tyr—Pro |
| Dynorphin | Tyr—Gly—Gly—Phe—Leu—Arg—Arg—Ile—Arg—Pro |
| Ph-8P (Dynorphin [1-8]) | Tyr—Gly—Gly—Phe—Leu—Arg—Arg—Ile |

The effective amount of endogenous peptide to be administered will vary depending on the circumstances and end result desired. Generally, the dose ranges that can be used therapeutically are from about 0.001 to about 30 mg/kg. Preferably, dosage rates from about a quarter of a miligram of enkephalin per kilogram of body weight to as low as about $10^{-14}$ mg/kg are employed. The method of treatment and administration can be by any of the known routes, including but not limited to: oral, i.v., i.m., s.c., aerosol, nasal, ophthalmic, or vaginal suppositories and the like. The enkephalins and endorphins can be used singly or in combination, or in combination with other known chemotherapeutic agents for the treatment of all forms of neoplastic activity or related conditions. Further, the present invention is viewed as being directly applicable to all mammalian/animal species.

Having thus described and exemplified the preferred embodiments with a certain degree of particularity, it is to be understood that the invention is not to be limited to the embodiments set forth herein for purposes of exemplification, but is to be limited only by the scope of the attached claims, including a full range of equivalents to which each element thereof is entitled.

I claim:

1. A process for inhibiting tumorous growth comprising the step of treating said tumorous growth, in vivo, with an endogenous endorphin.

2. A process of claim 1 wherein said endogenous endorphin is selected from the group consisting of beta-endorphin [61-91] and peptides of which beta-endorphin [61-91] is the precursor.

3. A process of claim 1 wherein said endogenous endorphin is selected from the group consisting of methionine-enkephalin, leucine-enkephalin, [arg$^6$]-leucine-enkephalin, alpha-neo-endorphin, beta-neo-endorphin, dynorphin, PH-8P (dynorphin [1-8]), and beta-endorphin.

4. A process of claim 1 wherein said endogenous endorphin is leucine-enkephalin.

5. A process of claim 1 wherein said endogenous endorphin is methionine-enkephalin.

6. A process of claim 4 wherein said enkephalin is administered in the range from about 0.001 to about 30 mg/kg.

7. A process of claim 5 wherein said enkephalin is administered in the range from about 0.001 to about 30 mg/kg.

8. A process for stimulating the natural immune system resisting tumorous growth comprising the step of treating the tumorous growth, in vivo, with an endogenous endorphin.

9. A process of claim 8 wherein said endogenous endorphin is selected from the group consisting of beta-endorphin [61-91] and peptides of which beta-endorphin [61-91] is the precursor.

10. A process of claim 8 wherein said endogenous endorphin is selected from the group consisting of methionine-enkephalin, leucine-enkephalin, [arg$^6$]-leucine-enkephalin, alpha-neo-endorphin, beta-neo-endorphin, dynorphin, PH-8P (dynorphin [1-8]), and beta-endorphin.

11. A process of claim 8 wherein said endogenous endorphin is leucine-enkephalin.

12. A process of claim 8 wherein said endogenous endorphin is methionine-enkephalin.

13. A process of claim 11 wherein said enkephalin is administered in the range from about 0.001 to about 30 mg/kg.

14. A process of claim 12 wherein said enkephalin is administered in the range from about 0.001 to about 30 mg/kg.

15. A process for the therapeutic treatment of cancer comprising the step of administering an effective dosage of an endogenous endorphin.

16. A process of claim 15 wherein said endogenous endorphin is selected from the group consisting of the following table:
Met-enkephalin
Leu-enkephalin
(Arg$^6$)-Leu-enkephalin
(Arg$^6$)-Met-enkephalin
(Lys$^6$)-Met-enkephalin
(Arg$^6$-Arg$^7$)-Met-enkephalin
(Arg$^6$-Phe$^7$)-Met-enkephalin
(Arg$^6$-Gly$^7$-Leu$^8$)-Met-enkephalin
Alpha-Neo-endorphin
Beta-Neo-endorphin
Dynorphin
Ph-8P(Dunorphin(1-8)).

17. A process of claim 15 wherein said endogenous endorphin is leucine-enkephalin.

18. A process of claim 15 wherein said endogenous endorphin is methionine-enkephalin.

19. A process of claim 17 wherein said enkephalin is administered in the range from about 0.001 to about 30 mg/kg.

20. A process of claim 18 wherein said enkephalin is administered in the range from about 0.001 to about 30 mg/kg.

21. A process of claim 15 wherein endogenous endorphin is administered in a dosage range from about 0.25 mg/kg to about $10^{-14}$ mg/kg.

22. A process of claim 16 wherein endogenous endorphin is administered in a dosage range from about 0.25 mg/kg to about $10^{-14}$ mg/kg.

23. A process of claim 17 wherein endogenous endorphin is administered in a dosage range from about 0.25 mg/kg to about $10^{-14}$ mg/kg.

24. A process of claim 18 wherein said leucine-enkephalin is administered in a dosage range from about 0.25 mg/kg to about $10^{-14}$ mg/kg.

* * * * *